(12) United States Patent
Boyle et al.

(10) Patent No.: US 7,704,274 B2
(45) Date of Patent: Apr. 27, 2010

(54) IMPLANTABLE GRAFT AND METHODS OF MAKING SAME

(75) Inventors: Christopher T. Boyle, San Antonio, TX (US); Denes Marton, San Antonio, TX (US); Christopher E. Banas, San Antonio, TX (US)

(73) Assignee: Advanced Bio Prothestic Surfaces, Ltd., Dallas, TX (US)

( * ) Notice: Subject to any disclaimer, the term of this patent is extended or adjusted under 35 U.S.C. 154(b) by 885 days.

(21) Appl. No.: 10/672,695

(22) Filed: Sep. 26, 2003

(65) Prior Publication Data

US 2004/0098094 A1 May 20, 2004

Related U.S. Application Data

(60) Provisional application No. 60/414,209, filed on Sep. 26, 2002.

(51) Int. Cl.
*A61F 2/06* (2006.01)
(52) U.S. Cl. ..................... 623/1.13; 623/1.39
(58) Field of Classification Search ................ 623/1.13
See application file for complete search history.

(56) References Cited

U.S. PATENT DOCUMENTS

| 4,073,999 A | 2/1978 | Bryan et al. ............ 428/311 |
|---|---|---|
| 4,510,182 A | 4/1985 | Cornils et al. ........... 427/162 |
| 4,657,544 A | 4/1987 | Pinchuk .................. 623/1 |
| 4,665,906 A | 5/1987 | Jervis .................... 128/92 |
| 4,751,099 A | 6/1988 | Niino et al. .............. 427/34 |
| 4,846,834 A | 7/1989 | von Recum et al. ....... 623/11 |
| 5,049,251 A | 9/1991 | Inoue .................... 204/192 |
| 5,061,914 A | 10/1991 | Busch et al. ............. 337/140 |
| 5,084,151 A | 1/1992 | Vallana ................ 204/192.11 |
| 5,133,845 A | 7/1992 | Vallana et al. ............. 204/192 |
| 5,190,546 A | 3/1993 | Jervis .................... 606/78 |
| 5,207,709 A | 5/1993 | Picha .................... 623/11 |
| 5,242,710 A | 9/1993 | Claar et al. .............. 427/248 |
| 5,277,933 A | 1/1994 | Claar et al. .............. 427/248 |
| 5,358,615 A | 10/1994 | Grant et al. ............ 204/192.15 |

(Continued)

FOREIGN PATENT DOCUMENTS

CA 2512311 A1 * 11/1995

(Continued)

OTHER PUBLICATIONS

"Liquid Sources for Chemical Vapor Deposition of Group 6 Metals and Metal Nitrides" by Gordon, et al., www.techtransfer.harvard.edu/cgi-bin/TALSearch.cgi?full_report=1&case=3, Case No. 1709.

(Continued)

*Primary Examiner*—Corrine M McDermott
*Assistant Examiner*—Christopher D Prone
(74) *Attorney, Agent, or Firm*—J. Peter Paredes; David G. Rosenbaum; Rosenbaum & Silvert, P.C.

(57) ABSTRACT

The present invention relates to an implantable endoluminal graft comprised of a microporous thin-film covering having a plurality of openings and a structural support element underlying and physically attached to the microporous thin-film covering, the microporous thin-film covering having shape memory properties.

30 Claims, 29 Drawing Sheets

U.S. PATENT DOCUMENTS

| | | | |
|---|---|---|---|
| 5,370,684 A | 12/1994 | Vallana et al. | 623/1 |
| 5,387,247 A | 2/1995 | Vallana et al. | 623/2 |
| 5,421,955 A | 6/1995 | Lau et al. | 216/48 |
| 5,455,100 A | 10/1995 | White | 428/131 |
| 5,477,864 A | 12/1995 | Davidson | 128/771 |
| 5,482,574 A | 1/1996 | Goldstein | 148/517 |
| 5,508,116 A | 4/1996 | Barrett | 428/567 |
| 5,514,154 A | 5/1996 | Lau et al. | 606/195 |
| 5,540,820 A | 7/1996 | Terakado et al. | 204/192.3 |
| 5,545,210 A | 8/1996 | Hess et al. | 623/1 |
| 5,569,295 A | 10/1996 | Lam | 606/198 |
| 5,578,149 A | 11/1996 | DeScheerder | 148/563 |
| 5,593,442 A | 1/1997 | Klein | 623/1 |
| 5,597,378 A | 1/1997 | Jervis | 606/78 |
| 5,597,458 A | 1/1997 | Sanchez, Jr. | 204/192.3 |
| 5,603,721 A | 2/1997 | Lau et al. | 606/195 |
| 5,605,714 A | 2/1997 | Dearnaley et al. | 427/2.24 |
| 5,607,445 A | 3/1997 | Summers | 606/198 |
| 5,607,463 A | 3/1997 | Schwartz et al. | 623/1 |
| 5,609,629 A | 3/1997 | Fearnot et al. | 623/1 |
| 5,624,508 A | 4/1997 | Flomenblit et al. | 148/510 |
| 5,628,788 A | 5/1997 | Pinchuk | 623/1 |
| 5,630,840 A | 5/1997 | Mayer | 623/1 |
| 5,635,144 A | 6/1997 | Aklufi | 422/186.05 |
| 5,647,858 A | 7/1997 | Davidson | 604/264 |
| 5,649,951 A | 7/1997 | Davidson | 606/198 |
| 5,649,977 A | 7/1997 | Campbell | 623/1 |
| 5,656,036 A | 8/1997 | Palmaz | 623/12 |
| 5,683,453 A | 11/1997 | Palmaz | 623/1 |
| 5,685,961 A | 11/1997 | Pourrezaei et al. | 204/192 |
| 5,690,670 A | 11/1997 | Davidson | 606/198 |
| 5,723,219 A | 3/1998 | Kolluri | 428/411.1 |
| 5,725,573 A | 3/1998 | Dearnaley et al. | 623/2 |
| 5,728,150 A | 3/1998 | McDonald et al. | 623/1 |
| 5,728,158 A | 3/1998 | Lau et al. | 623/12 |
| 5,733,303 A | 3/1998 | Israel et al. | 606/198 |
| 5,735,896 A | 4/1998 | Amon et al. | 623/11 |
| 5,744,515 A | 4/1998 | Clapper | 523/113 |
| 5,765,418 A | 6/1998 | Rosenberg | 72/47 |
| 5,772,864 A | 6/1998 | Moller et al. | 205/73 |
| 5,776,161 A | 7/1998 | Globerman | 606/194 |
| 5,780,807 A | 7/1998 | Saunders | 219/121 |
| 5,782,908 A | 7/1998 | Cahalan et al. | 623/1 |
| 5,782,910 A | 7/1998 | Davidson | 623/3 |
| 5,788,558 A | 8/1998 | Klein | 451/136 |
| 5,811,151 A | 9/1998 | Hendricks et al. | 427/2.24 |
| 5,824,045 A | 10/1998 | Alt | 623/1 |
| 5,824,049 A | 10/1998 | Ragheb | 623/1 |
| 5,824,056 A | 10/1998 | Rosenberg | 623/1 |
| 5,840,009 A | 11/1998 | Fischell et al. | 600/3 |
| 5,843,117 A | 12/1998 | Alt et al. | 606/194 |
| 5,843,120 A | 12/1998 | Israel et al. | 606/198 |
| 5,843,289 A | 12/1998 | Lee et al. | 204/192 |
| 5,849,206 A | 12/1998 | Amon et al. | 216/63 |
| 5,853,419 A | 12/1998 | Imran | 606/191 |
| 5,855,600 A | 1/1999 | Alt | 623/1 |
| 5,855,802 A | 1/1999 | Acciai et al. | 216/8 |
| 5,855,955 A | 1/1999 | Claar et al. | 427/248.1 |
| 5,858,556 A | 1/1999 | Eckert et al. | 428/586 |
| 5,866,113 A | 2/1999 | Hendricks et al. | 424/78.17 |
| 5,868,782 A | 2/1999 | Frantzen | 606/198 |
| 5,873,904 A | 2/1999 | Ragheb et al. | 623/1 |
| 5,876,432 A | 3/1999 | Lau et al. | 623/1 |
| 5,879,370 A | 3/1999 | Fischell et al. | 606/198 |
| 5,891,507 A | 4/1999 | Jayaraman | 427/2.25 |
| 5,895,406 A | 4/1999 | Gray et al. | 606/198 |
| 5,899,935 A | 5/1999 | Ding | 623/1 |
| 5,907,893 A | 6/1999 | Zadno-Azizi | 29/6.1 |
| 5,913,896 A | 6/1999 | Boyle et al. | 623/1 |
| 5,919,225 A | 7/1999 | Lau et al. | 623/1 |
| 5,925,063 A | 7/1999 | Khosravi | 606/200 |
| 5,932,036 A | 8/1999 | Fukai | 148/670 |
| 5,932,299 A | 8/1999 | Katoot | 427/508 |
| 5,938,682 A | 8/1999 | Hojeibane et al. | 606/198 |
| 5,938,697 A | 8/1999 | Killion et al. | 623/1 |
| 5,945,153 A | 8/1999 | Dearnaley | 427/2.12 |
| 5,951,881 A | 9/1999 | Rogers et al. | 216/41 |
| 5,954,724 A | 9/1999 | Davidson | 606/76 |
| 5,955,588 A | 9/1999 | Tsang et al. | 536/21 |
| 5,962,138 A | 10/1999 | Kolluri et al. | 428/411.1 |
| 5,968,091 A | 10/1999 | Pinchuk et al. | 623/1 |
| 5,972,018 A | 10/1999 | Israel et al. | 606/198 |
| 5,972,027 A | 10/1999 | Johnson | 623/1 |
| 5,984,905 A | 11/1999 | Dearnaley et al. | 604/265 |
| 6,007,573 A | 12/1999 | Wallace et al. | 623/1 |
| 6,013,054 A | 1/2000 | Yan | 604/96 |
| 6,013,855 A | 1/2000 | McPherson et al. | 623/11 |
| 6,015,429 A | 1/2000 | Lau et al. | 623/1 |
| 6,016,693 A | 1/2000 | Viani et al. | 73/105 |
| 6,019,784 A | 2/2000 | Hines | 623/1 |
| 6,022,370 A | 2/2000 | Tower | 606/194 |
| 6,027,526 A | 2/2000 | Limon et al. | 623/1 |
| 6,033,433 A | 3/2000 | Ehr et al. | 623/1 |
| 6,042,597 A | 3/2000 | Kveen et al. | 606/198 |
| 6,042,605 A | 3/2000 | Martin et al. | 623/1 |
| 6,056,776 A | 5/2000 | Lau et al. | 623/1 |
| 6,059,808 A | 5/2000 | Boussignac | 606/191 |
| 6,066,167 A | 5/2000 | Lau et al. | 623/1 |
| 6,066,168 A | 5/2000 | Lau et al. | 623/1 |
| 6,066,169 A | 5/2000 | McGuinness | 623/1.16 |
| 6,071,305 A | 6/2000 | Brown et al. | 623/1 |
| 6,086,773 A | 7/2000 | Dufresne et al. | 216/8 |
| 6,096,175 A | 8/2000 | Roth | 204/192 |
| 6,103,320 A | 8/2000 | Matsumoto et al. | 427/535 |
| 6,106,642 A | 8/2000 | DiCarlo et al. | 148/563 |
| 6,113,705 A | 9/2000 | Ohashi et al. | 118/730 |
| 6,113,750 A | 9/2000 | Shinmura et al. | 204/192.15 |
| 6,113,982 A | 9/2000 | Claar et al. | 427/248.1 |
| 6,120,536 A | 9/2000 | Ding et al. | 623/11.43 |
| 6,120,847 A | 9/2000 | Yang et al. | 427/335 |
| 6,124,523 A | 9/2000 | Banas et al. | 623/11 |
| 6,126,761 A | 10/2000 | DeHaven et al. | 148/518 |
| 6,126,793 A | 10/2000 | Sugiyama et al. | 204/192.23 |
| 6,136,159 A | 10/2000 | Buckfeller et al. | 204/192.13 |
| 6,136,258 A | 10/2000 | Wang et al. | 264/514 |
| 6,149,742 A | 11/2000 | Carpenter et al. | 148/563 |
| H1924 H | 12/2000 | Zabinski et al. | 204/192.16 |
| 6,156,052 A | 12/2000 | Richter et al. | 606/191 |
| 6,156,373 A | 12/2000 | Zhong et al. | |
| 6,173,672 B1 | 1/2001 | Shapard, Jr. | 118/723 |
| 6,190,404 B1 | 2/2001 | Palmaz et al. | 623/1.15 |
| 6,190,407 B1 | 2/2001 | Ogle et al. | 623/1.51 |
| 6,194,088 B1 | 2/2001 | Yoshida et al. | 428/660 |
| 6,202,304 B1 | 3/2001 | Shatz | 29/896.6 |
| 6,203,505 B1 | 3/2001 | Jalisi et al. | 600/585 |
| 6,207,536 B1 | 3/2001 | Matsumoto et al. | 438/478 |
| 6,217,952 B1 | 4/2001 | Sugiyama et al. | 427/577 |
| 6,231,923 B1 | 5/2001 | Teverovsky et al. | 427/248.1 |
| 6,238,491 B1 | 5/2001 | Davidson et al. | 148/237 |
| 6,240,616 B1 | 6/2001 | Yan | 29/527.2 |
| 6,245,104 B1 | 6/2001 | Alt | 623/1.46 |
| 6,248,401 B1 | 6/2001 | Chiang et al. | 427/255.7 |
| 6,253,441 B1 | 7/2001 | Wheat et al. | 29/527.2 |
| 6,258,121 B1 | 7/2001 | Yang et al. | 623/1.46 |
| 6,258,182 B1 | 7/2001 | Schetky et al. | 148/402 |
| 6,258,417 B1 | 7/2001 | Goswami et al. | 427/452 |
| 6,261,320 B1 | 7/2001 | Tam et al. | 623/1.15 |
| 6,264,595 B1 | 7/2001 | Delfino et al. | 600/1 |
| 6,264,598 B1 | 7/2001 | Armini | 600/3 |
| 6,264,687 B1 | 7/2001 | Tomonto | 623/1.16 |
| 6,267,782 B1 | 7/2001 | Ogle et al. | 623/1.1 |
| 6,267,867 B1 | 7/2001 | Olson | 205/640 |
| 6,274,014 B1 | 8/2001 | Matsumoto et al. | 204/298.11 |
| 6,280,467 B1 | 8/2001 | Leonhardt | 623/1.16 |

| | | | |
|---|---|---|---|
| 6,284,316 B1 | 9/2001 | Sandhu et al. ......... 427/255.391 |
| 6,287,277 B1 | 9/2001 | Yan .......................... 604/96.01 |
| 6,287,329 B1 | 9/2001 | Duerig et al. .............. 623/1.11 |
| 6,287,430 B1 | 9/2001 | Matsumoto et al. .... 204/192.26 |
| 6,287,435 B1 | 9/2001 | Drewery et al. ........ 204/298.09 |
| 6,287,628 B1 | 9/2001 | Hossainy et al. ............. 427/2.3 |
| 6,290,720 B1 | 9/2001 | Khosravi et al. ........... 623/1.13 |
| 6,290,721 B1 | 9/2001 | Heath ........................ 623/1.15 |
| 6,293,966 B1 | 9/2001 | Frantzen .................... 623/1.15 |
| 6,293,967 B1 | 9/2001 | Shanley ..................... 623/1.15 |
| 6,299,604 B1 | 10/2001 | Ragheb et al. .............. 604/265 |
| 6,299,755 B1 | 10/2001 | Richter ...................... 205/238 |
| 6,306,141 B1 | 10/2001 | Jervis .......................... 606/78 |
| 6,306,276 B1 | 10/2001 | Nobe et al. ................. 205/238 |
| 6,309,414 B1 | 10/2001 | Rolando et al. ........... 623/1.15 |
| 6,312,456 B1 | 11/2001 | Kranz et al. ............... 623/1.13 |
| 6,312,463 B1 | 11/2001 | Rourke et al. ............. 623/1.39 |
| 6,315,708 B1 | 11/2001 | Salmon et al. ................. 600/3 |
| 6,315,794 B1 | 11/2001 | Richter ...................... 623/1.34 |
| 6,322,585 B1 | 11/2001 | Khosravi et al. ........... 623/1.11 |
| 6,327,772 B1 | 12/2001 | Zadno-Azizi ................ 29/557 |
| 6,331,190 B1 | 12/2001 | Shokoohi et al. .......... 623/1.22 |
| 6,331,191 B1 | 12/2001 | Chobotov .................. 623/1.44 |
| 6,334,868 B1 | 1/2002 | Ham ......................... 623/1.13 |
| 6,346,119 B1 | 2/2002 | Kuwahara et al. .......... 623/1.13 |
| 6,348,066 B1 | 2/2002 | Pinchuk et al. ............. 623/1.16 |
| 6,361,637 B2 | 3/2002 | Martin et al. ............... 156/187 |
| 6,383,214 B1 | 5/2002 | Banas et al. ................ 623/1.14 |
| 6,387,122 B1 | 5/2002 | Cragg ........................ 623/1.16 |
| 6,458,152 B1 | 10/2002 | Khosravi et al. ........... 623/1.13 |
| 6,585,764 B2 * | 7/2003 | Wright et al. .............. 623/1.42 |
| 2001/0000043 A1 | 3/2001 | Israel et al. ................. 606/198 |
| 2001/0000188 A1 | 4/2001 | Lenker et al. |
| 2001/0003146 A1 | 6/2001 | Jalisi et al. ................. 600/585 |
| 2001/0009169 A1 | 7/2001 | Kajiwara et al. ............ 148/563 |
| 2001/0009220 A1 | 7/2001 | Mizuno et al. .............. 427/569 |
| 2001/0011158 A1 | 8/2001 | Howland .................... 600/585 |
| 2001/0019847 A1 | 9/2001 | Ori et al. |
| 2001/0021570 A1 | 9/2001 | Lin et al. .................... 438/455 |
| 2001/0021870 A1 | 9/2001 | Edwin et al. |
| 2001/0025131 A1 | 9/2001 | Edwin et al. |
| 2001/0032013 A1 | 10/2001 | Marton |
| 2001/0037144 A1 | 11/2001 | Kim et al. |
| 2001/0037146 A1 | 11/2001 | Lau et al. ................... 623/1.16 |
| 2001/0039449 A1 | 11/2001 | Johnson et al. |
| 2001/0047200 A1 | 11/2001 | White et al. ............... 623/1.15 |
| 2001/0047201 A1 | 11/2001 | Cox et al. .................. 623/1.16 |
| 2001/0055647 A1 | 12/2001 | Tamura et al. .............. 427/177 |
| 2001/0055654 A1 | 12/2001 | Halpern ...................... 427/600 |
| 2002/0013616 A1 | 1/2002 | Carter et al. |
| 2002/0042649 A1 | 4/2002 | Schaldach et al. .......... 623/1.15 |
| 2002/0165600 A1 | 11/2002 | Banas et al. ............... 623/1.11 |

FOREIGN PATENT DOCUMENTS

| | | |
|---|---|---|
| DE | 1452370 | 3/1974 |
| DE | 199 37 638 | 5/2001 |
| EP | 0 400 947 | 12/1990 |
| EP | 0 442 303 | 8/1991 |
| FR | 2 777 771 | 10/1999 |
| JP | 51055724 | 5/1976 |
| JP | 61-88135 | 5/1986 |
| JP | 10072319 | 10/1999 |
| RU | 2110606 | 5/1998 |
| WO | 97/07257 | 2/1997 |
| WO | 97/44692 | 11/1997 |
| WO | 98/13537 | 4/1998 |
| WO | 98/45506 | 10/1998 |
| WO | 99/16385 | 4/1999 |
| WO | 99/23977 | 5/1999 |
| WO | 99/62432 | 12/1999 |
| WO | 00/04204 | 1/2000 |
| WO | 00/18327 | 4/2000 |
| WO | 00/54704 | 9/2000 |
| WO | 00/55181 | 9/2000 |
| WO | 01/21851 | 3/2001 |
| WO | 01/21852 | 3/2001 |
| WO | 01/35865 | 5/2001 |
| WO | 01/37892 | 5/2001 |
| WO | 01/43790 | 6/2001 |
| WO | 01/49340 | 7/2001 |
| WO | 01/53559 | 7/2001 |
| WO | 01/55473 | 8/2001 |
| WO | 01/56502 | 8/2001 |
| WO | 01/85064 | 11/2001 |
| WO | 01/91918 | 12/2001 |

OTHER PUBLICATIONS

"Fabrication of Small-Scale Coils and Bands as Photomasks on Optical Fibers for Generation of In-Fiber Gratings, Electromagnets as Micro-NMR Coils, Microtransformers, and Intra-Vascular Stents" www.techtransfer.harvard.edu/cgi-bin/TALSearch. cgi?full_report=1&case=72, Case No. 1263.

"Reactions of Biological Cells to Nanostructures", by Curtis, et al., AVS 46$^{th}$ International Symposium Paper BI-WeM2 (Oct. 27, 1999).

"Biocompatibility of Cardiac Cells on Silane-Modified Surfaces" AVS 46$^{th}$ International Symposium, Paper BI-WeM5 (Oct. 27, 1999).

"Biofunctionalization of Surfaces with Peptide Amphilphiles" AVS 46$^{th}$ International Symposium, Paper No. BI-WeM7 (Oct. 27, 1999).

"Plasma Copolymer Surfaces for Cell Culture" AVS 46$^{th}$ International Symposium, Paper No. Paper BI-WeM9 (Oct. 27, 1999).

"Plasma Co-polymer Surfaces for the Controlled Adsorption of Common Proteins" AVS 46$^{th}$ International Symposium, Paper No. BI-FrM2 (Oct. 29, 1999).

"Biofilm—Titanium Chemistry of Adhesion Using X-ray Photoelectron Spectroscopy" AVS 46$^{th}$ International Symposium, Paper No. BI-FrM8.

"Nanoscale Patterning of Golf for Attachment of Supported Lipid Bilayers" AVS 46$^{th}$ International Symposium, Paper No. BI-FrM10.

"Focused Ion Beam Non-Fabrication", http://www.glue.umd.edu/~astan/avs04.htm.

"Amorphous Carbon and C:N Thin Films" http://www.glue.umd.edu/~astan/avs01.htm.

Multilayer Ceramic/Metallic Coatings by Ion Beam-Assisted, Electron Beam Physical Vapor (EB-PVD) Deposition, Penn State Appled Research Laboratory, pp. 1-4 (1997).

"Benefits From Diamond-Like Coated Stainless Steel Stents", http://www.phytis.com/stents0.htm, pp. 1-2.

"Adhesion of Bovine Serum Albumin on Coated DLC (Diamond-Like) and Uncoated ($SiO_2$ / $TiO_2$) Sensor Chips", http://www.phytis.com/stent4.htm, pp. 1-2.

"Flow Cytometric Investigation", http://www.phytis.com/stent6.htm, pp. 1-3.

"Pre-clinical and Clinical Evaluation", http://www.phytis.com/stent2.htm, pp. 1B2.

"The New Phytis Stent", http://www.phytis.com/stent1.htm, pp. 1-2.

"Invulnerability and Resistance of DLC-Coating", http://www.phytis.com/stent3.htm, pp. 1-3.

"Material In Use and Its Biocompatibility", http://www.phytis.com/stent5.htm, pp. 1-2.

"Expertise Concerning the Implementation of the Phytis Diamon as Stent Performed at the Institute for Experimental Medicine (IEM)", http://www.phytis.com/stent9.htm, pp. 1.

"Phytis L.D.A. Home Page information", http://www.phytis.com/content/htm, pp. 1-15.

"Risk Analysis of Stents With a Diamond-Like Coated Surface For Use in Prosthetic Implants", http://www.phytis.com/risk.htm, pp. 1-6.

"Directions for Use, Diamond AS200 Stent", http://www.phytis.com/direcuse.htm, pp. 1-8.

"Stents: Literature", http://www.phytis.com/liter.htm, pp. 1-8.

"The Effects of Ion Irradiation of NiTi Shape Memory Alloy Thin Films" by F. Goldberg and E. Knystautas, *Proceedings of the Second*

*International Conference on Shape Memory and Superelastic Technologies Asilomar Conference Center*, Pacific Grove, California, USA, pp. 177-182 (1997).

"Constitutive Parts of a Shape Memory Alloy Titanium Nickel Thin Film Catheter" by L. Buchaillot, et al., *Proceedings of the Second International Conference on Shape Memory and Superelastic Technologies Asilomar Conference Center*, Pacific Grove, California, USA, pp. 183-199 (1997).

"The Effect of HCD Technological Factors on the NiTi SMA Film Thickness" by Q. Pingshan, et al., *Proceedings of the Second International Conference on Shape Memory and Superelastic Technologies Asilomar Conference Center*, Pacific Grove, California, USA, pp. 173-176 (1997).

"Microstructure ofTi-Rich TiNi Thin Films" by A. Ishida, et al., *Proceedings of the Second International Conference on Shape Memory and Superelastic Technologies Asilomar Conference Center*, Pacific Grove, California, USA, pp. 161-166 (1997).

"Thin Film Shape Memory Alloy Microactuators"by TiNi Alloy Company (online).

"Progress in Thin Film Shape Memory Microactuators" by Johnson, et al., www.sma-mems.com/recent.htm (Overview), pp. 1-5.

"A Concise History of Vacuum Coating Technology, Part 2: 1940 to 1975" by D. Mattox, www.svc.org/HistoryofVac2.html, pp. 1-15.

"Model Surfaces for Studying and Controlling the Adhesion of Cells" by M. Mrksich, AVS $47^{th}$ International Symposium, Invited Paper No. BI+EL-TuA1 (Oct. 3, 2000).

"Cell Response to Chemically and Topographically Modified Surfaces" by D.S. Sutherland, et al., AVS $47^{th}$ International Symposium, Paper No. BI+EL-TuA3 (Oct. 3, 2000).

"The Nanomechanical Properties of Thin Films" by J.E. Houston, AVS $47^{th}$ International Symposium, Paper No. TF-TuA1 (Oct. 3, 2000).

"Anomalous Plastic and Elastic Behaviors of Sputter-deposited TiNi with 10 or 20 Inserted Thin Al Layers Evaluated by Nanoindentation" by E. Kusano, et al., AVS $47^{th}$ International Symposium, Paper No. TF-TuA3 (Oct. 3, 2000).

"Recent Progress in the Application of Thin Film Shape Memory Alloys" by A.D. Johnson and J.D. Busch, *Proceedings of the First International Conference on Shape Memory and Superelastic Technologies Asilomar Conference Center*, Pacific Grove, California, USA, pp. 299-310 (1994).

"Thin-film Processing of TiNi Shape Memory Alloy" by J.A. Waker and K.J. Gabriel, *Sensors and Actuators*, A21-A23, pp. 243-246 (1990).

"Sputter-deposition of TiNi, TiNiPd and TiPd films displaying the two-way shape-memory effect" by E. Quandt, et al., *Sensors and Actuators*, A 53, pp. 434-439 (1996).

"Applications of Shape-Memory Alloy Thin Films" by A.D. Johnson and V.V. Martynov, *Proceedings of the Second International Conference on Shape Memory and Superelastic Technologies Asilomar Conference Center*, Pacific Grove, California, USA, pp. 1-8 (1997).

"Role of Bio-Physiochemical Parameters in Cell Adhesion and Rolling-Simulation Analysis" by A. Alshorman, T. David and P. Walker, *BED*, vol. 50, pp. 209-210 (2001).

"Thin Film Shape Memory Microvalues with Adjustable Operation Temperature" by M. Kohl, D. Kittman, E. Quandt and B. Winzek, *Sensors and Actuators*, vol. 83, pp. 214-219 (2000).

"A Temperature-Controlling Device for Refrigerators" by M.C. Shin, K.K. Jee and B.C. Ku, *Proceedings of the First International Conference of Shape Memory and Superelastic Technologies*, pp. 305-310 (1994).

"The Experimental Use of Steel Mesh Tubes for the Replacement of Arterial Segments" by Larry, Banning G., M.D., et al, *Presented at the Third Scientific Meeting of the North American Chapter of the International Society of Angiology*, Atlantic City, NJ, pp. 69-75, Jun. 4, 1955.

Abstract: "Relative importance of bombardment energy and intensity in ion plating" by K.S. Fancey, C.A. Porter and A. Matthews, *Journal of Vacuum Science & Technology A: Vacuum, Surfaces, and Films*, Mar. 1995, vol. 13, Issue s, pp. 428-435.

Abstract: "Oriented nickel-titanium shape memory alloy films prepared by annealing during deposition" by K. Gisser, J. Bussh and A. Johnson and A. Ellis, *Applied Physics Letters*, Oct. 1992, vol. 61, Issue 14, pp. 1632-1634.

Abstract: "Vacuum conditions for sputtering thin film TiNi" by A. Peter Jardine, *Journal of Vacuum Science & Technology A: Vacuum, Surfaces, and Films*, May 1995, vol. 13, Issue 3, pp. 1058-1062.

Multicomponent Film Deposition by Target Biasing, *IBM Technical Disclosure Bulletin*, pp. 1-2 (Jul. 1980).

"Shape Memory Properties in NiTi Sputter-deposited Film", J.D. Busch and A.D. Johnson, *J Appl. Phys*, vol. 68, No. 12, pp. 6224-6226 (Dec. 15, 1990).

"Endothelial Cell Organization on Micropatterned Protein Surfaces" by R. Daw, et al., AVS $47^{th}$ International Symposium, Paper No. BI-WeP21 (Oct. 4, 2000).

"Tissue Formation of Hepatocytes on Micro-Porous Films of Polylactide" by T. Nishikawa, et al., AVS $47^{th}$ International Symposium, Paper No. BI+EL-TuA10 (Oct. 3, 2000).

"Sputtering Targets High-Quality Thin Film Materials" by AMETEK Specialty Metal Products online at www.ametek84.com/fd-sputtering.html, pp. 1-3.

"The influence of ion irradiation during film growth on the chemical stability of film/substrate systems" by W. Ensinger, *Surface and Coatings Technology*, vol. 80, pp. 35-48 (1996).

"The Characteristics of NiTi HCD-Deposited SMA Films" by H. Weixin, et al., *Proceedings of the Second International Conference on Shape Memory and Superelastic Technologies Asilomar Conference*, Pacific Grove, California, USA, pp. 167-172 (1997).

* cited by examiner

Longitudinal Axis

Longitudinal Axis

IMPLANTABLE GRAFT AND METHODS OF MAKING SAME

CROSS-REFERENCE TO RELATED APPLICATIONS

This application claims priority from U.S. Provisional Application Ser. No. 60/414,209 filed Sep. 26, 2002 and is related to the following, commonly assigned U.S. Patent Applications, which are hereby incorporated by reference: U.S. Ser. No. 09/745,304, filed Dec. 22, 2000 which is a divisional of U.S. Ser. No. 09/443,929 filed Nov. 19, 1999 and issued as U.S. Pat. No. 6,379,383 on Apr. 30, 2002, U.S. Ser. No. 09/707,685 filed Nov. 7, 2000, U.S. Ser. No. 10/135,316 filed Apr. 29, 2002 U.S. Ser. No. 10/135,626 filed Apr. 29, 2002 and U.S. Ser. No. 10/120,800 filed Apr. 11, 2002, published as US2003004567 on Jan. 2, 2003.

BACKGROUND OF THE INVENTION

The present invention generally relates to the field of implantable medical devices intended to maintain patency of anatomical passageways, such as those found in the cardiovascular, lymphatic, endocrine, renal, gastrointestinal and/or reproductive systems of mammals. More particularly, the present invention relates to grafts that are designed for endoluminal delivery using a delivery catheter and minimally invasive surgical techniques. The present invention generally comprises grafts or graft assemblies that are fabricated entirely of biocompatible metals or of biocompatible materials that exhibit biological response and material characteristics substantially the same as biocompatible metals, such as for example composite materials.

Conventional endoluminal stents and stent-grafts are frequently used after a percutaneous transluminal angioplasty (PTA) or percutaneous transluminal coronary angioplasty (PTCA) procedure which dilitates an occluded, obstructed or diseased anatomical passageway to provide structural support and maintain the patency of the anatomical passageway. An example of this is the post-angioplasty use of intravascular stents to provide a structural support for a blood vessel and reduce the incidence of restenosis. A principal, but non-limiting, example of the present invention are endovascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma. Stent-grafts are delivered and deployed under similar circumstances and are utilized to maintain patency of an anatomic passageway, for example, by reducing restenosis following angioplasty, or when used to exclude an aneurysm, such as in aortic aneurysm exclusion applications.

While the use of endoluminal stents has successfully decreased the rate of restenosis in angioplasty patients, it has been found that a significant restenosis rate continues to exist in spite of the use of endoluminal stents. It is generally believed that the post-stenting restenosis rate is due, in major part, to the non-regrowth of the endothelial layer over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis.

At present, most endoluminal stents are manufactured of metals that fail to promote redevelopment of a healthy endothelium and/or are known to be thrombogenic. In order to increase the healing and promote endothelialization, while maintaining sufficient dimensional profiles for catheter delivery, most stents minimize the metal surface area that contacts blood. Thus, in order to reduce the thrombogenic response to stent implantation, as well as reduce the formation of neointimal hyperplasia, it would be advantageous to increase the rate at which endothelial cells form endothelium proximal and distal to the stent situs, migrate onto and provide endothelial coverage of the luminal surface of the stent which is in contact with blood flow through the vasculature.

Current stent-grafts are essentially endoluminal stents with a discrete covering on either or both of the luminal and abluminal surfaces of the stent that occludes the open spaces, or interstices, between adjacent structural members of the endoluminal stent. It is known in the art to fabricate stent-grafts by covering the stent with endogenous vein or a synthetic material, such as woven polyester known as DACRON, or with expanded polytetrafluoroethylene. Additionally, it is known in the art to cover the stent with a biological material, such as a xenograft or collagen. A primary purpose for covering stents with grafts is to reduce the thrombogenic effect of the stent material. However, the use of conventional graft materials has not proven to be a complete solution to enhancing the healing response of conventional stents.

U.S. Pat. No. 6,312,463 describes a variation of a prosthesis in that the prosthesis includes a tubular element that is a thin-walled sheet having temperature-activated shape memory properties. The tubular element is supported by a support element that includes a plurality of struts. The tubular element is described as a thin-walled sheet preferably having of a coiled-sheet configuration with overlapping inner and outer sections.

There still remains a need in the art for an implantable endoluminal graft that provides the necessary structural component to support an endoluminal wall and is biocompatible and prevents or limits the occurrence of restenosis.

SUMMARY OF THE INVENTION

An aspect of the present invention provides an implantable graft that includes a microporous thin film covering comprised of a metallic or pseudometallic material and an underlying structural support made of a metallic or pseudometallic material. The microporous metallic or pseudometallic thin film covering is also described in co-pending, commonly assigned U.S. patent application Ser. Nos. 10/135,316 and 10/135,626, both filed on Apr. 29, 2002, both of which are hereby expressly incorporated by reference as describing the microporous thin film covering. The microporous thin film covering is physically attached to the underlying structural support, preferably by welding, suturing, or other commonly known methods of attachment at particular interfacial points. While both the microporous thin film covering and the underlying structural support may be fabricated from many different materials, in accordance with a preferred aspect of the present invention, both the microporous thin film covering and the underlying structural support are fabricated from metallic or pseudometallic materials having shape memory and/or superelastic properties. More preferably, the metal used to fabricate both the microporous thin film covering and the underlying structural support of inventive implantable endoluminal graft is Nitinol. The underlying structural support, without the microporous thin film covering, is similar to implantable devices known as a "stents." The underlying structural support can assume any commonly known geometries in the art that possess requisite hoop strength, circumferential compliance and longitudinal flexibility for both endoluminal delivery and acting as an in vivo prosthesis. In a preferred embodiment, the structural support element adopts a geometry that includes at least a pair of cylindrical elements and interconnecting members that join adjacent cylindrical elements at nearly identical angular points along the circumference of the cylindrical elements.

In another aspect of the present invention, an implantable graft includes a microporous thin film covering comprised of a metallic material which has shape memory and/or pseudoelastic properties and a structural support element underlying the microporous thin film covering. "Pseudoelastic properties" is used herein to refer to the ability of the metallic material to undergo "pseudoelastic deformation". In a preferred aspect, the structural support element has shape memory properties that allow the structural support element to undergo a phase transition from martensite to austenite phase at body temperature. During this phase transition, the structural support element self-expands from an initial, delivery diameter to an enlarged expanded diameter for its intended in vivo use. The shape memory expansion of the structural support element exerts a radially expansive force upon the microporous thin film covering, thereby causing the microporous thin film to radially expand with the structural support element. While the expansion of the microporous thin film appears to be plastic, because the microporous thin film is a shape memory material, the expansion is actually fully recoverable above the transition temperature of the material, and is, therefore, "pseudoplastic".

In still another aspect of the present invention, an implantable endoluminal graft is comprised of a microporous thin film covering comprised of a shape memory alloy having an austenite phase transition temperature, $A_s$, greater than 37° C. and a structural support element underlying the microporous thin film covering that is comprised of a shape memory alloy that has an austenite phase transition temperature less than 0° C. Thus, in both the delivery diameter and the implanted expanded diameter, the microporous thin film remains in a martensite state, while the structural element undergoes a phase transition from martensite to austenite at body temperature.

Another aspect of the present invention is an implantable endoluminal graft wherein the structural support element is physically attached to the microporous thin film covering at least one point of contact between the microporous thin film covering and the structural support element. Preferably, the at least one point of contact is located at either near a proximal end or distal end of the microporous thin film covering and corresponding end of the structural support element. Even more preferably, the at least one point of contact is located at near a distal end of the microporous thin film covering and structural support element. The physical attachment of the structural support element to the microporous thin film covering is accomplished by using a spot weld, a suture, adhesive, or other means of physically joining the two elements. Preferably, the attachment is accomplished using a spot weld.

In another aspect of the present invention, the implantable endoluminal graft includes a structural support element comprised of a cylindrical element having a sinusoidal pattern with alternating peaks and valleys. Furthermore, interconnecting members join adjacent cylindrical elements either peak-to-peak or valley-to-valley. Another aspect of the present invention includes cylindrical elements that have widths that are narrower at and near the apices than at other segments of the cylindrical elements.

In another aspect of the present invention, the implantable endoluminal graft includes a structural support element comprised of a cell that is defined by adjacent interconnecting members and sections of the pair of cylindrical elements connecting the adjacent interconnecting members, the cell comprised of a pair of peaks or a pair of valleys.

In another aspect of the present invention, the implantable endoluminal graft includes a microporous thin film covering comprised of a uniform pattern of openings throughout the surface of the microporous thin film covering. The openings can be selected from common geometric shapes including a circle, triangle, ellipsoid, diamond, star, clover, rectangle, square, or straight or curved lines.

The structural support member may consist of any type of structural member and is preferably generally tubular in configuration, and has an inner or luminal wall and an outer or abluminal wall and a central lumen passing along the longitudinal axis of the structural support member. The structural support member may be comprised of a wide variety of geometric configurations and constructions, as are known in the art. For example, the structural support member may assume a balloon expandable slotted configuration of U.S. Pat. Nos. 4,733,665, 4,739,762, 4,776,337 or 5,102,417 or the structural support member may be configured as a plurality of self-expanding interwoven wire members or it may assume any of the wall geometries disclosed in Serruys, P. W., Kutryk, M. J. B., *Handbook of Coronary Stents*, $3^{rd}$ Ed. (2000). Each of the structural support member designs, structural support member materials, structural support member material characteristics, e.g., balloon expandable, self-expanding by spring tension of the material, self-expanding by shape memory properties of the structural support member material, or self-expanding by superelastic properties of the structural support member material are well known to one of ordinary skill in the art and may be used with the implantable graft of the present invention.

An aspect of the present invention is the fabrication of the implantable endoluminal graft using various techniques that can create a blood contact surface that has controlled heterogeneities therein. More particularly, this aspect of the present invention provides an implantable endoluminal graft that is made of a material having controlled heterogeneities in its atomic profile, material composition, grain composition, grain phase, grain size, or surface topography, along the blood flow surface of the implantable endoluminal graft.

Another aspect of the present invention is a method for making the implantable graft which employs vacuum deposition methodologies, such as those employed in the microelectronics fabrication arts. For example sputtering, physical vapor deposition, ion beam-assisted evaporative deposition or the like may be used to create the microporous thin film covering and the structural support member components of the implantable graft device. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber is typically argon. The substrate may be either stationary or moveable; either rotated about its longitudinal axis, moved in an X-Y plane, planatarily or rotationally moved within the deposition chamber to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant structural supports or microporous thin film covering, both in the context of spatial orientation of patterns of regions of relative thickness and thinness, such as by varying the thickness of the film over its length to impart different mechanical characteristics under different delivery, deployment or in vivo environmental conditions.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as carbon, aluminum or organic based materials, such as photoresists, may be deposited intermediate the substrate and the structural support member and the sacrificial layer removed by melting, chemical means, ablation, machining or other suitable means to free the structural support member from the substrate.

The resulting device may then be subjected to post-deposition processing to modify the crystalline structure, such as by annealing, or to modify the surface topography, such as by etching to expose a heterogeneous surface of the device.

Alternate deposition processes which may be employed to form the structural support member in accordance with the present invention are cathodic arc, laser ablation, and direct ion beam deposition. As known in the metal fabrication arts, the crystalline structure of the deposited film affects the mechanical properties of the deposited film. These mechanical properties of the deposited film may be modified by post-process treatment, such as by, for example, annealing.

Materials to make the implantable endoluminal graft are chosen for their biocompatibility, mechanical properties, i.e., tensile strength, yield strength, and their ease of deposition include, without limitation, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

The implantable endoluminal graft device of the present invention is formed entirely of metal or pseudometal material that exhibits improved endothelialization and healing response as compared to that associated with using conventional synthetic polymeric graft materials.

DETAILED DESCRIPTION OF THE PREFERRED EMBODIMENTS

Figure 1:
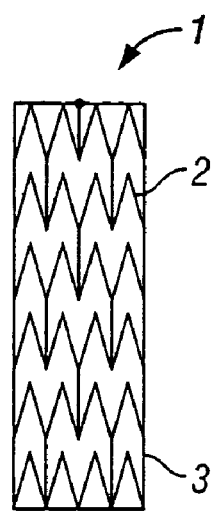
FIG. 1 is a plan view of an embodiment of the implantable device its delivery diameter.

In accordance with the present invention, an implantable endoluminal graft is provided that is comprised of two main features: a microporous thin film covering and an underlying structural support member, which are physically connected to one another. The implantable endoluminal graft has a delivery profile that allows for uncomplicated entry and passage throughout an anatomical passageway, more particularly a vascular system. Additionally, the implantable endoluminal graft is formed from a shape memory material, preferably nitinol, which permits the graft to expand in vivo to support a lumen wall.

The term "pseudometal" and "pseudometallic material," as used herein, is defined as a biocompatible material which exhibits biological response and material characteristics substantially the same as biocompatible metals. Examples of pseudometallic materials include, for example, composite materials, ceramics, quartz, and borosilicate. Composite materials are composed of a matrix material reinforced with any of a variety of fibers made from ceramics, metals, or polymers. The reinforcing fibers are the primary load carriers of the material, with the matrix component transferring the load from fiber to fiber. Reinforcement of the matrix material may be achieved in a variety of ways. Fibers may be either continuous or discontinuous. Reinforcement may also be in the form of particles. Examples of composite materials include those made of carbon fibers, boron fibers, boron carbide fibers, carbon and graphite fibers, silicon carbide fibers, steel fibers, tungsten fibers, graphite/copper fibers, titanium and silicon carbide/titanium fibers.

The term "Elastic Deformation," as used herein, is defined as a deformation caused by an applied load that is completely recoverable upon removal of the applied load. The elastic limit of a traditional metal is typically less than 1% strain.

The term "Plastic Deformation," as used herein, is defined as deformation caused by an applied load that cannot be completely recovered upon removal of the load because bonds have been broken.

The term "Pseudoelastic Deformation," as used herein, is defined as a deformation caused by an applied load that is completely recoverable upon removal of the load and the limit of which is characterized by being significantly larger than the elastic limit of a traditional metal (8% strain in the case of nitinol). This phenomenon is caused by a load or stress induced phase change that is reversible upon removal of the load.

The term "Pseudoplastic Deformation," as used herein, is defined as a deformation caused by an applied load that requires some other action besides load removal, such as the application of heat, for complete recovery of the deformation. In pseudoplastic deformations, bonds have not been broken but, instead, have been reoriented (detwinned in the case of martensitic nitinol).

A stress-strain curve for austenitic nitinol in which a sample is taken all the way to failure at a temperature above $A_f$ (finish of Austenitic transformation) can be separated into the following regions: elastic deformation of austenite, pseudoelastic deformation of austenite to stress induced martensite, elastic deformation of the stress induced martensite, plastic deformation of the stress induced martensite and fracture. Removal of the load at any point before the onset of plastic deformation of the stress induced martensite will result in complete recovery of the deformation.

Nitinol is in the thermally induced martensite state if the material deformed at temperatures below $M_f$ (finish of Martensitic transformation) and subsequently kept below $A_s$ (onset of austenitic transformation) or restrained from recovering its programmed shape above $A_s$. A stress-strain curve for martensitic nitinol in which a sample is taken all the way to failure at a temperature above below $A_s$ can be separated into the following regions: elastic deformation of thermally induced martensite, pseudoplastic deformation of thermally induced martensite via detwinning, elastic deformation of the detwinned thermally induced martensite, plastic deformation of the detwinned thermally induced martensite and fracture. Removal of the load at any point before the onset of plastic deformation of the detwinned thermally induced martensite will result in complete recovery of the deformation when heated above $A_f$.

In a preferred embodiment of the present invention, the $A_s$ temperature of the NiTi thin film microporous thin film covering is above body temperature. The microporous thin film covering is in a thermally induced martensite phase at its delivery diameter in a delivery catheter and, because the microporous thin film covering is approximately the same diameter as the ID of the catheter sheath, the microporous thin film covering experiences virtually no deformation while in the catheter. Upon delivery, the microporous thin film covering experiences a pseudoplastic radial deformation under the influence of shape memory expansion of the structural support.

In a preferred embodiment of the present invention, the $A_f$ temperature of the NiTi structural support element is below body temperature. The structural support element is brought to a temperature below $M_f$ and loaded into the catheter at a temperature below $A_s$ such that the structural support element is in a thermally induced martensite phase before deformation from to the delivery diameter occurs. The structural support element is pseudoplastically deformed during crimping and is considered to be in the pseudoplastically deformed, thermally induced martensite phase until deployment in the body by removing the constraining force at a temperature above $A_f$.

Concerning the fabrication and physical characteristic of the present invention, it is important to contemplate the blood protein interaction with surfaces of endoluminal devices because it appears to be an initial step in a chain of events leading to tissue incorporation of the endovascular device, and eventually to re-endothelialization along the surface of the device. An aspect of the present invention is based, in part, upon the relationship between surface energy of the material used to make the endoluminal device and protein adsorption at the surface of the endoluminal device. It has been found that a relationship exists between surface free energy and protein adsorption on metals commonly used in fabrication of endoluminal devices. In addition, specific electrostatic forces resident on the surface of metal endoluminal stents have been found to influence blood interactions with the graft surface and the vascular wall.

Another important factor to consider is electrostatic forces, which play a significant role in limiting interaction between the natural endothelial lining of the vasculature, which is highly electronegative, and a majority of plasma proteins and blood borne cells that also bear a net electronegative charge. Upon introduction of an implantable endoluminal device into the vasculature, the electrostatic surface charge on surfaces of the thin film covering and the structural support which are in contact with blood, will also interact with plasma proteins, blood borne cells and the healthy endothelial lining at the site of the device. Current implantable endoluminal devices are typically fabricated of one of the following metals: 316L stainless steel, nitinol, gold, tantalum or titanium. These examples exhibit poor endothelialization in cases where implanted endoluminal devices are made of these materials and result in restenosis.

In order to determine the cause for failure of re-endothelialization, the surface properties of metals commonly used in endoluminal devices, including grafts, stents and stent-grafts, were evaluated for free energy and electrostatic charge. The relationship between free energy at the surface of an endoluminal device material and protein adsorption was evaluated by preparing five separate samples as flat, square 1×1 cm pieces: electropolished 316L stainless steel, nitinol with two different surface preparations: electropolished and electropolished/heat-treated, gold, tantalum and titanium. The electrostatic charges at the surface of each of these metals were evaluated by atomic force microscopy (AFM) to examine the possible electrostatic heterogeneity of the device's metal surface.

In addition, the microtopology of the endoluminal device material surface will have an effect on protein binding, both during initial protein binding to the material surface as well as during the cascade of protein binding necessary for endothelialization of the material surface. Thus, surface features such as homogeneous atomic profile and material grain size will affect both primary binding of a protein, whether a blood borne protein or a cellular surface protein, at, for example, hydrophobic regions of the protein and affect secondary binding of the hydrophilic binding region of the protein upon protein bending and attraction to surface regions of the material.

Surface Free Energy Testing

Five samples of metals and metal alloys commonly used to make stents were prepared as flat, square 1×1 cm pieces: electropolished 316L stainless steel, nitinol with two different surface preparations: electropolished and electropolished/heat-treated, gold, tantalum and titanium. All sample pieces underwent a standardized 5 step ultrasonic cleaning process as follows: initial bath in detergent (20% Extran 1000, VWR Science, West Chester, P.C.) followed by distilled water rinse, methanol rinse, acetone rinse and distilled water rinse, in sequence.

Each of the five samples were exposed to single protein solutions at physiological concentrations of albumin (Armour Pharmaceutical Company, Kankakee, Ill.), fibrinogen (Sigma Chemical Co., St. Louis, Mo.) and fibronectin (ICN Biomedicals, Aurora, Ohio). Each protein solution was spiked with a low concentration of the corresponding radiolabeled protein as follows: $I^{125}$ albumin (Amersham Pharmacia biotech, Arlington Heights, Ill.), $I^{125}$ fibrinogen or $I^{125}$ fibronectin (ICN Pharmaceuticals, Inc., Irvine, Calif.). The estimated overall activity of the solutions was $0.64 \times 10^6$ dpm/ml. Static protein adsorption was determined by immersing the material pieces in the iodinated protein solution for 2 hours at 37E C. After removal from the solution, the activity on the specimens was assessed in an automated well counter. Then, each piece was rinsed in phosphate buffered saline solution for 24 hours at 37E C and the activity of the remaining protein on the surface was reassessed. Each experiment was repeated three times.

Surface energy of all materials was determined by the advancing contact angle measurement using a video contact angle system (VCAS 2500 XE, AST systems, Billerica, Mass.) and calculated by the harmonic mean method. Water, formamide and xylene were used to compute total surface energy and the polar and dispersive components. Ten video-captures per second of the advancing fluid droplet/solid interface were obtained for water and formamide and 65 captures per second for xylene. All experiments were repeated 4 times.

Results of Surface Free Energy Testing

Total surface energy of 316L stainless steel, electropolished (ep) nitinol, electropolished and heat treated (epht) nitinol, gold, tantalum and titanium, ranged from 32.8 dyne/cm for ep nitinol to 64.6 dyne/cm or 316L stainless steel with an average of 43.9±4.8 dyne/cm. Of the polar and dispersive, or non-polar, components of the total surface energy of each metal, the non-polar component is the largest with an average polar/non-polar ratio of 0.21±0.07.

Protein binding was found to be relatively uniform for all metal surfaces studied. Of the three proteins tested, albumin adsorption was lower than fibronectin on all metals, and also lower than fibrinogen except for adsorption on gold and titanium. The fraction of protein removed after elution was higher for albumin than for either fibrinogen or fibronectin for all metal surfaces except for gold and titanium.

The marked correlation between the surface energy measurements and the amount of protein bound on the surface indicates a relationship between protein binding and the magnitude of hydrophobic surface forces.

Electrostatic Force Testing

Flat 1×1 cm square pieces (0.159 cm thick) of electropolished 316L stainless steel, nitinol with two different surface preparations: electropolished and electropolished/heat-treated, gold, tantalum and titanium were used for determination of relative metal surface electrostatic forces. All sample pieces underwent a standardized 5 step ultrasonic cleaning process as follows: initial bath in detergent (20% Extran 1000, VWR Science, West Chester, P.C.) followed by distilled water rinse, methanol rinse, acetone rinse and distilled water rinse, in sequence. After cleaning, the metal samples were placed in the AFM for acquisition of electrostatic force curves under dilute saline solution (pH 7.0). Ten electrostatic force curves were performed at each of 5 sites on each metal sample. A total of five samples of each different metal were measured.

Possible electrostatic heterogeneity was examined by obtaining force volume arrays. Force volume arrays were obtained by scanning a defined area of each surface by taking 32 curves per line, with 32 lines per area being scanned. A relative height by color was assigned to the electrostatic force level for each measurement taken. The result was a mosaic which depicts both the overall level of electrostatic force as well as a map of the surface charge variability within a given area.

Results of Electrostatic Force Testing

Examination of the color level of the force volume images, it was noted that the color for the volume images for gold and stainless steel are relatively homogeneous compared to the image for Nitinol. Additionally, gold and stainless steel appear to have similar electrostatic force levels that on average would be higher than the level obtained for the Nitinol image after averaging in the darker, or lower, measurements depicted.

Since the AFM used a negatively charged silicon nitride tip, as the tip is brought close to a negatively charged surface, double layer forces cause the tip to bend away from the surface and depart from a linear patter of descent to the surface. It is that departure that is measured as repulsive force. On the other hand, where the surface exhibits a positive charge relative to the tip, an attractive force is present which causes the tip to bend toward the surface and, also, depart from a linear descent to the surface. Thus, the force volume images indicate that both stainless steel and gold exhibit net repulsive forces whereas the curve for Nitinol exhibits a slight attractive force for the pixel selected. The cross-hair on the Nitinol curve represents a dark pixel on the force volume curve. Selection of a light colored pixel in the force volume image would have yielded a repulsive curve, demonstrating the heterogeneity of the electropolished Nitinol surface.

Additionally, the difference in the intensity of surface-associated force between electropolished Nitinol and either gold or stainless steel is further substantiated by examining the relative z-position or distance from the surface that the silicon nitride tip first starts to bend and deflect away from the surface. In the case of gold and stainless steel, repulsive forces extend out to approximately 70 nm from the surface, but are only detected at 17 nm from the Nitinol surface.

Oxidation of the Nitinol surface, obtained by heat treating the Nitinol, yielded a more homogeneous force volume image than the electropolished Nitinol, and was similar to that observed with stainless steels, gold and titanium. Similarly, the distance from the oxidized surface at which force was detected increased to 90 nm from the 17 nm measured for the electropolished surface.

In comparing the results of total surface energy testing with electrostatic charge testing, there does not appear to be a direct correlation between surface energy and electrostatic charge. However, when total surface energy is compartmentalized into polar and nonpolar components, the polar component of surface energy exhibits a significant correlation to electrostatic surface forces. This correlation suggests that both surface energy and homogeneity of surface electrostatic charge are significant to protein adsorption and endothelialization.

These foregoing findings have direct applicability to implantable endoluminal device manufacture. In accordance with an aspect of the present invention there is provided an implantable endoluminal graft that is fabricated of a material having surfaces characterized by having controlled heterogeneities at the blood contact surface of the graft. Current manufacturing methods for fabricating endoluminal stents and grafts fail to achieve the desired material properties of the present invention. Presently, stents are made by machining a series of slots or patterns to accommodate radial expansion into a stainless steel or nickel-titanium metal hypotube, or by weaving wires into a self-expanding matrix. According to the present invention, an implantable endoluminal graft having controlled heterogeneities on at least one surface thereof is provided by fabricating the entire or individual components of the inventive endoluminal graft, including the structural support and the thin film covering by vacuum deposition techniques in which the process parameters of deposition are controlled to control the surface heterogeneities in the inventive endoluminal graft. Suitable deposition methodologies, as are known in the microelectronic fabrication arts and incorporated herein by reference, are plasma vapor deposition, chemical vapor deposition, physical vapor deposition and ion implantation which are utilized to impart a metal layer onto the stent and/or graft pattern which has a high amorphous content.

Turning now to the accompanying figures, FIGS. 1-4 illustrate one preferred embodiment of the present invention. FIGS. 5-41 illustrate alternative embodiments of the present invention.

Figure 2:
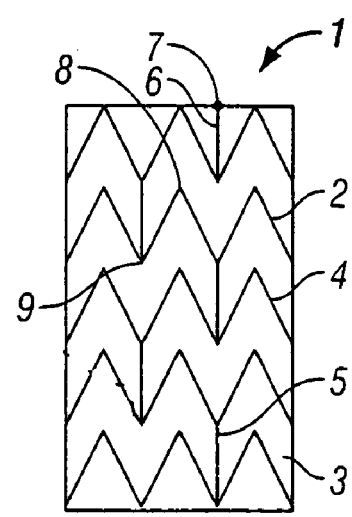
FIG. 2 is a plan view of an embodiment of the implantable device in its expanded or intended in vivo diameter.

FIGS. 1 and 2 show an implantable endoluminal graft 1 comprised of the structural support member 2 providing scaffolding for the microporous metal thin film covering 3. FIG.

1 shows the implantable endoluminal graft 1 in its delivery profile or unexpanded state. FIG. 2 shows the same implantable endoluminal graft 1 as it adopts its expanded state. In the expanded state, one can observe the cylindrical elements 4 and the interconnecting members 5 that form the structural support element 2. The microporous metal thin film covering 3 is attached to the structural support element 2 by attachment at a point on the terminal end 7 of a terminal interconnecting member 6. The terminal interconnecting member 6 may be at one or both ends of the structural support member 2, i.e., the proximal and/or distal ends of the implantable endoluminal graft 1; thereby allowing for attachment of the microporous metal thin film covering 3 at one or both ends thereof. Preferably, as shown in FIG. 2, the interconnecting member 6 is present on the distal end of the structural support element 2; thereby allowing for attachment of the microporous metal thin film covering 3 only on the distal end of the implantable endoluminal graft 1. The interconnecting members 5 connect adjacent cylindrical elements 4 to one another in a manner that maintains the cylindrical elements 4 in-phase with one another. In order to maintain an in-phase relationship between adjacent cylindrical elements 4, the interconnecting members 5 connect a cylindrical element 4 at either a peak 8 or a valley 9 and connect to the corresponding peak 8 or valley 9 on an adjacent cylindrical element 4.

Attachment of the microporous metal thin film covering 3 to the structural support element 2 at the terminal end 7 may be achieved by chemical, mechanical or thermal means. For example, the attachment can be achieved by welding, adhering using a biocompatible adhesive, or by forming interlocking mechanical members on opposing surfaces of the microporous metal thin film covering 3 and the structural support element 2. Preferably, attachment is accomplished by forming a spot weld at the terminal ends 7.

Figure 3:
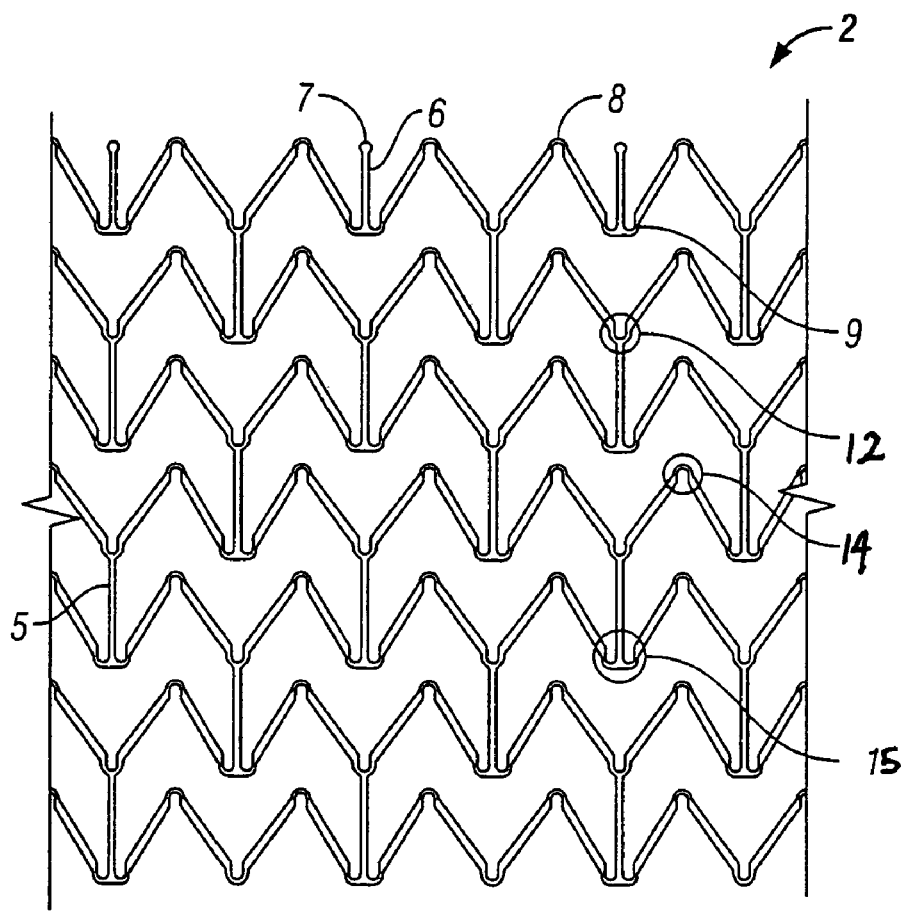
FIG. 3 is a plan view of a structural support element of a preferred embodiment of the implantable endoluminal device while in an expanded diameter.

FIG. 3 shows a structural support element 2 of an alternative preferred embodiment. This figure shows a structural support element 2 that is formed from cylindrical elements 4 attached to adjacent cylindrical elements 4 by interconnecting members 5. The interconnecting members 5 connect adjacent cylindrical elements 4 to one another in a manner that maintains the cylindrical elements 4 in-phase with one another. In order to maintain an in-phase relationship between adjacent cylindrical elements 4, the interconnecting members 5 connect a cylindrical element 4 at either a peak 8 or a valley 9 and connect to the corresponding peak 8 or valley 9 on an adjacent cylindrical element 4. The apices, which are the peaks 8 and valleys 9 of the cylindrical elements 4, are either attached to or not attached to interconnecting members 5. Opposing ends of each interconnecting member 5 are connected to adjacent cylindrical elements 4 at apices 12 and 15. The attachment between interconnecting members 5 and the adjacent cylindrical elements 4 forms a generally Y-shaped apex 20 and at an opposing end of the interconnecting member 5 forms a generally W-shaped apex 14. Finally, a generally U-shaped apex 14 is positioned without any interconnection member 5 and forms the intermediate apices between adjacent W-shaped apices 15.

Figure 3A:
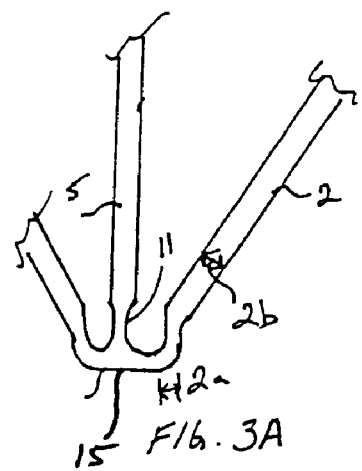
FIG. 3A is a fragmentary plan view of an alternate embodiment of an apex portion of a structural support member in accordance with the inventive implantable endoluminal device.

As illustrated in FIGS. 3 and 3A, and in accordance with a preferred embodiment of the present invention, it is advantageous to have a narrowed region 11 of each interconnecting member 5 at the junction position between the interconnecting member and the apex of the cylindrical member 4. Additionally, it is preferably that each apex 12, 14 and 15 of each cylindrical member 4 also be narrowed relative to the remaining section of the cylindrical member 4. In this manner, the width 2a of the material in the X-Y plane of the material at the apex is narrower than the width 2b of the material in the same X-Y plane of the remaining section of the structural support element 2. The narrowed region 11 and the narrowed region 2a of the apices are positioned in regions that are subjected to relatively higher strain during expansion of the structural support element 2 from its delivery diameter to its implanted diameter during endoluminal delivery and assist in relieving strain in these regions of the structural support element 2.

Additionally, the structural support element 2 can include additional features that can adjust its physical characteristics including longitudinal flexibility, radial expansion and hoop strength. The structural support element 2 can include reduced widths at the apices 8, 9, in both the cylindrical elements 4 and interconnecting members 5. This reduced width occurs in areas of increased stress, especially during radial expansion. During radial expansion, these high stress regions can experience cracks if the width is too large. Therefore, the width should be such that the high stress regions are able to meet the material strain, radial strength and expansible requirements of the structural support element. Additional flexibility of the structural support element can be provided by adding the generally U-shaped loop structures at the apices of the cylindrical elements. The generally U-shaped loop structures aid in unloading applied strain during radial expansion, thereby reducing the amount of stress transmitted to the remaining sections or struts of the cylindrical elements.

Alternative geometries are contemplated for the structural support elements 2. Such alternative geometries may include, for example, planar geometries for use as patches, frustroconical geometries such as for use as anchors for dental implants or other complex geometries such as for osteal implants.

Figure 4:
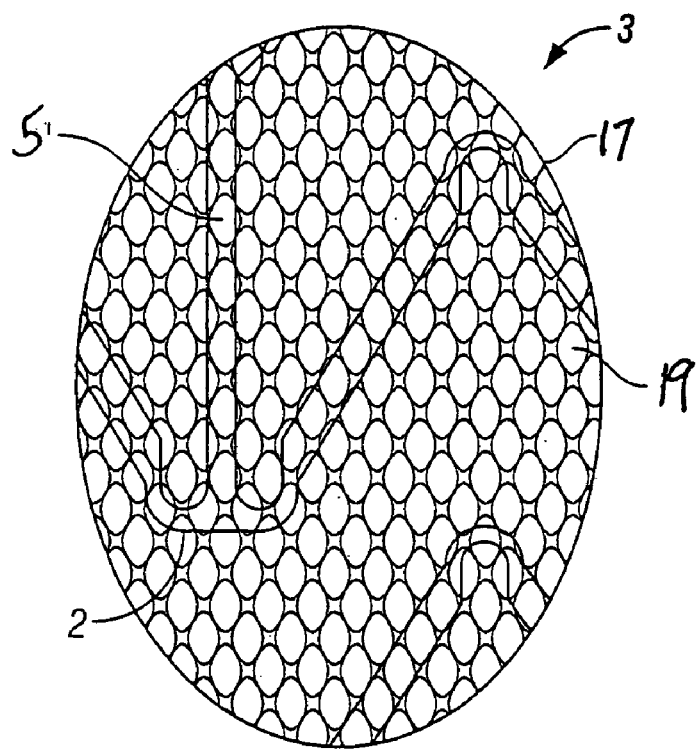
FIG. 4 is an exploded plan view of a microporous metal thin film covering of an embodiment of the implantable endoluminal device while in an expanded diameter.

FIG. 4 illustrates a fragmentary view of a segment of the structural support element 2 at an apex 15 of FIG. 3 covered by the inventive microporous metal thin film covering 3. The microporous metal thin film covering 3 consists generally of a thin film metal covering material 17 having a plurality of micro-openings 19. The plurality of openings 19 preferably has an open surface area within the range of 0.5 µm to 150 µm, with the total open surface area being between 0.001 to 90%. The openings 19 permit cellular and sub-cellular physiological matter, such as proteins, to pass through the openings 19. Both the size of the openings 19 and the total open area of the microporous metal thin film covering 17 may be selected in view of the following non-exclusive factors: the desired flexibility of the graft, the desired hoop strength of the graft, the desired degree of geometric enlargement due to deformation of the openings 19 and the desired delivery profile size. The plurality of openings 19 impart dimensional flexibility to the microporous metal thin film covering 17, compressibility and expandability along the longitudinal axis of the implantable endoluminal graft 1, while also permitting compliance, foldabilty and expandability in the radial axis of the implantable endoluminal graft 1. The plurality of openings 19 is preferably provided in a pattern array in order to maximize the physical properties of the microporous metal thin film covering 17 and, hence, the resulting inventive implantable endoluminal graft 1. For example, the pattern array may be provided to selectively enhance longitudinal flexibility while reinforcing against radial compliance.

Alternative embodiments of the present invention can have a varying size of each of the plurality of openings in the microporous metal thin film covering so that cellular migration occurs through each opening, without permitting fluid flow there through. In this manner, for example, blood cannot flow through the plurality of openings (in the deformed or un-deformed state), but various cells or proteins may freely pass through the plurality of openings to promote graft healing in vivo. For some applications, moderate amounts of fluid flow through the plurality of deformed or un-deformed microperforations may be acceptable. For example, endoluminal saphenous vein grafts may be fabricated with openings in the microporous metal thin film covering that serve the dual function of permitting transmural endothelialization while also excluding biological debris, such as thrombus from passing through the wall thickness of the graft, effectively excluding detrimental matter from entering the circulation. In this example, each of the plurality of openings, in either their deformed or undeformed state, may exceed several hundred microns.

Those skilled in the art will understand that a direct relationship exists between the size of pores and the overall ratio of expansion or deformability of an implantable graft. Generally, therefore, it is appreciated that pore sizes must increase in order to increase the effective attainable degree of expansion or deformation of the graft. Further descriptions of microporous metal thin film covering structures and, in particular, opening sizes are described in U.S. patent application Ser. Nos. 10/135,316 and 10/135,626, which are hereby incorporated by reference.

Figure 5:
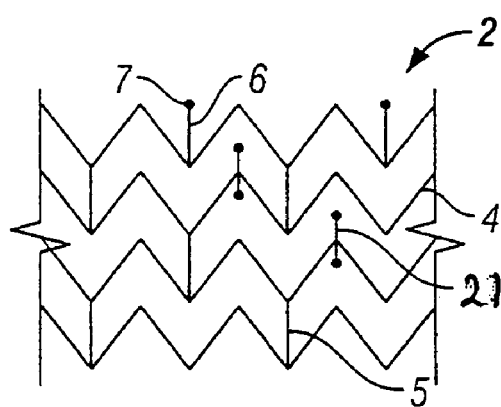
FIG. 5 is a plan view of a structural support element of an alternative embodiment of the inventive implantable endoluminal device.

A structural support element 2 of an alternative preferred embodiment is illustrated in FIG. 5. The interconnecting members 5 connect adjacent cylindrical elements 4 to one another in a manner that maintains the cylindrical elements 4 in-phase with one another. In order to maintain an in-phase relationship between adjacent cylindrical elements 4, the interconnecting members 5 connect adjacent cylindrical elements 4 at either a peak 8 or a valley 9 of a first cylindrical element 4 and connect to the corresponding peak 8 or valley 9 on a second cylindrical element 4. This pattern of connection forms either a peak-to-peak or a valley-to-valley interconnection. In addition to the terminal end 7 of the terminal interconnecting member 6, the structural support element 2 also has attachment members 50 attached to apices of cylindrical elements 4 other than the terminal cylindrical elements 4. The attachment members 21 resemble the terminal interconnecting member 6 but are located internally and attach to the microporous metal thin film covering 17 as illustrated in FIG. 4. By providing additional attachment points, this preferred embodiment of the implantable endoluminal graft 1 allows for closer interaction and higher degree of correspondence between the structural support element 2 and the microporous metal thin film covering 17. The greater degree of correspondence results in less slippage or folding of the microporous metal thin film covering 17 relative to the structural support element 2.

Figure 6:
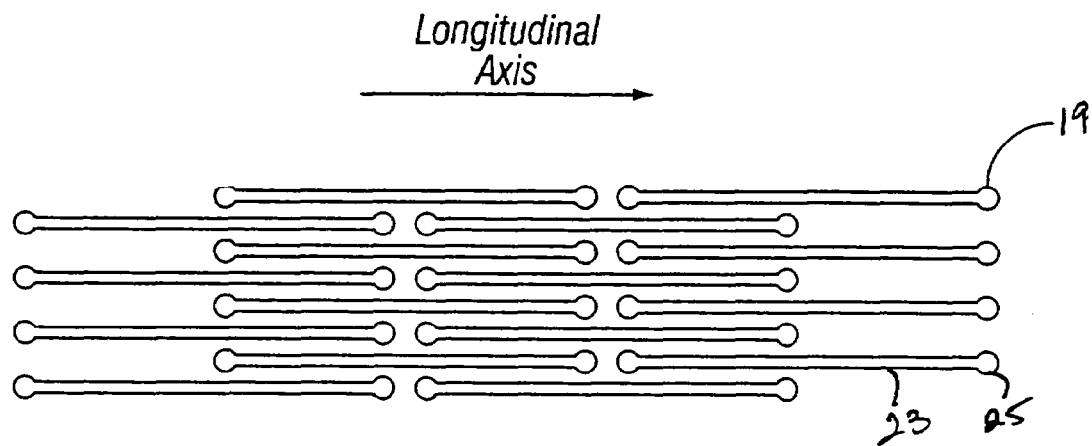
FIG. 6 is a plan view of a pattern of openings for a microporous metal thin film covering in accordance with a preferred embodiment of the present invention.

FIG. 6 illustrates a pattern of a plurality of openings 19 for a microporous metal thin film covering 17 in accordance with a preferred embodiment of the invention. Each of the plurality of openings 19 consists generally of a narrow longitudinal slot 23 having generally circular fillet openings 25 at opposing ends of each narrow longitudinal slot 23. It has been found preferable to provide the generally circular fillet openings 25 to enhance the ability of each of the narrow longitudinal slots 23 to widen and expand upon application of an expansive force perpendicular to the longitudinal axis of the microporous metal thin film covering 17 and of the narrow longitudinal slot 23. As depicted in FIG. 6, each narrow longitudinal slot 23 is in its closed state as would be the case in the unexpanded state of the microporous metal thin film covering 17 of the present invention. In accordance with this embodiment of the invention, each of the openings 19 have a longitudinal axis that is parallel to the longitudinal axis of the microporous metal thin film covering 17. The openings 19 are in a staggered formation, so that adjacent openings 19 are positioned with an offset that is approximately one-half the length of an adjacent opening 19. This staggered pattern of openings 19, together with both the size and shape of the openings 19, provides a predetermined ratio of expansion along with both radial compliance and longitudinal flexibility for the microporous metal thin film covering 17. The thickness of the microporous metal thin film covering 17 may be between about 0.1 µm to about 20 µm, with a preferred range being between about 1 µm to about 10 µm, and a most preferred thickness being between about 1 µm and about 4.5 µm.

Figure 7:
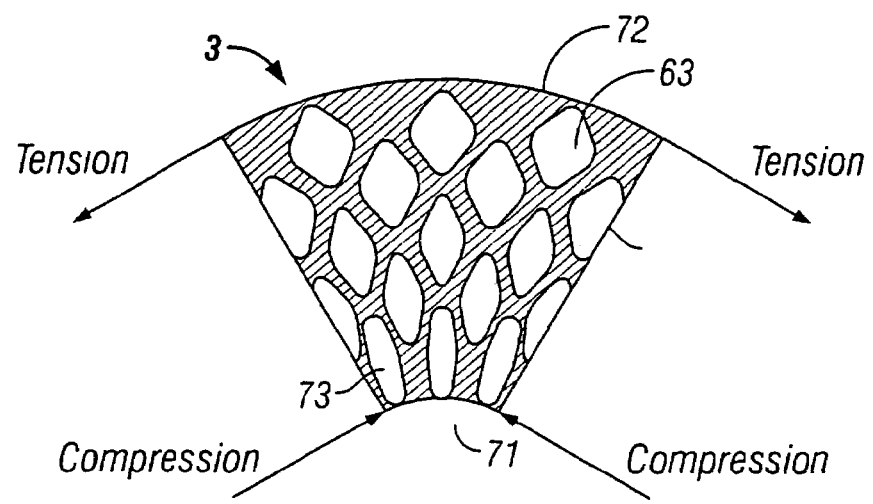
FIG. 7 is a plan view of a section of a microporous metal thin film covering of an embodiment of the present invention in a curved configuration depicting compliance of the microporous metal thin film covering.

The high degree of flexibility of the microporous metal thin film covering 17 is illustrated FIG. 7, which illustrates a segment of the microporous metal thin film covering 17 bent to traverse about 45 degrees. This configuration is contemplated to occur in curved regions of a body lumen, e.g., a curved portion of the vascular system. The implantable endoluminal graft undergoes curved configurations as it passes through a body lumen, which is not generally in a straight configuration; therefore, flexibility in the implantable endoluminal graft is important to traverse these regions without causing an impairment or injury to the lumenal system. In the curved configuration, the microporous metal thin film covering 3 is observed to have a compressed side 71 and an opposite, expanded side 72. Upon traversing the surface of the microporous metal thin film covering 3 perpendicular to the central axis of the implantable endoluminal graft 1, from the expanded side 72 to the compressed side 71, the openings 31 are observed to go from an about fully expanded opening 63 to a compressed opening 73, which undertakes a more elliptical form. A significant aspect of the present invention is that the plurality of openings 19 are capable of both expansion and contraction in response to either tensile forces or compressive forces exerted on the microporous metal thin film covering 3 and provide a high degree of compliance to resist buckling and wrinkling of the covering 3 surface as is typically found with conventional stent coverings.

Figure 8:
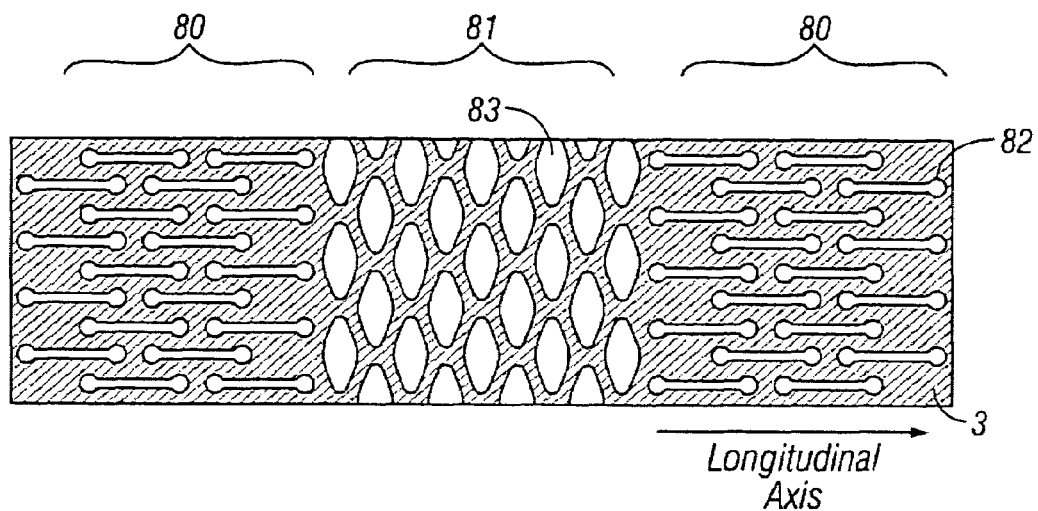
FIG. 8 is a plan view of a microporous metal thin film covering of an alternative embodiment of the present invention shown in unexpanded-longitudinally expanded-unexpanded regions.

FIG. 8 illustrates a microporous metal thin film covering 3 of an alternative embodiment having two closed sections 80 surrounding an open section 81. In each closed section 80, the openings are closed openings 82, which are in a closed, unexpanded state. In the open section 81, each of the openings 83 have been subjected to a longitudinally expansive force and have changed from a slot shaped opening like each of the closed openings 82 and have opened to a diamond-like shaped opening characteristic of being under tension. Each of the closed openings 82 are oriented parallel to the longitudinal axis of the microporous thin film covering 3 and, therefore, under a longitudinally oriented tensile load will not open. In contrast, each of the openings 83 have their longitudinal axis oriented perpendicular to the longitudinal axis of the microporous thin film covering 3 and a longitudinally oriented tensile load will open each of the openings 83.

FIGS. 9-26 illustrate alternate patterns of the microporous openings that may be used in the inventive microporous metal thin film covering 3 in accordance with alternate embodiments of the present invention. Each opening pattern has its own unique physical characteristics, including porosity, diffusion rate therethrough, radial and longitudinal compliance, longitudinal flexibility, ratio of both radial and longitudinal expansion relative to the unexpanded state, and surface flow rates (i.e., the rate of flow across the surface). A given opening pattern may be selected based upon criteria established for the particular situation requiring intervention, e.g., for saphenous vein grafting, coronary artery stenting, aortic aneurysm exclusion, etc.

Figure 9:
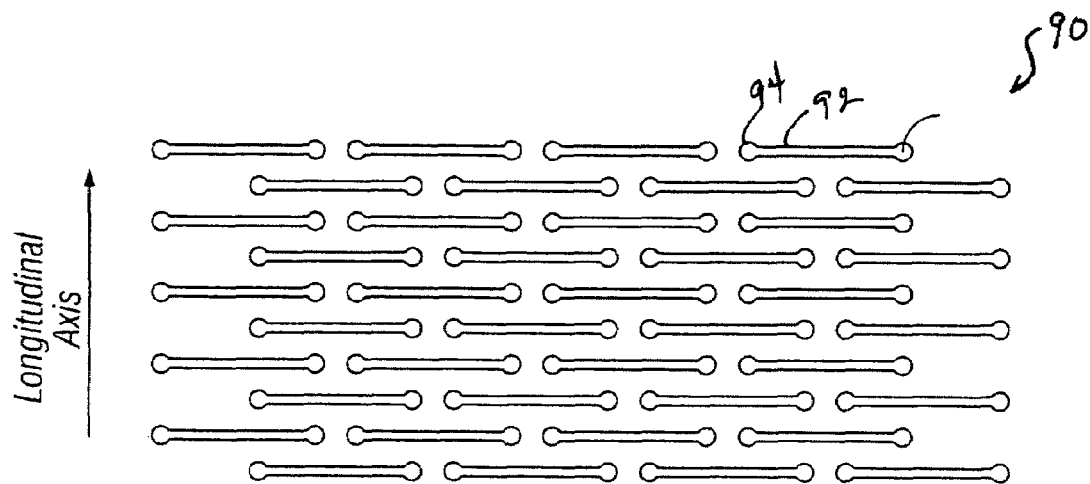
FIG. 9 is a plan view of a pattern of openings for a microporous metal thin film covering of an alternative embodiment of the present invention.

In FIG. 9, opening pattern 90 is illustrated in which each of the plurality of openings 92 are generally longitudinal slots with generally circular fillet openings 94 at opposing ends thereof. The longitudinal axis of each of the plurality of openings is perpendicular to the longitudinal axis of the microporous metal thin film covering such that longitudinal expansive properties are imparted to the metal thin film covering. Adjacent rows of the longitudinal slots 92 are staggered on approximately one-half length spacing.

Figure 10:
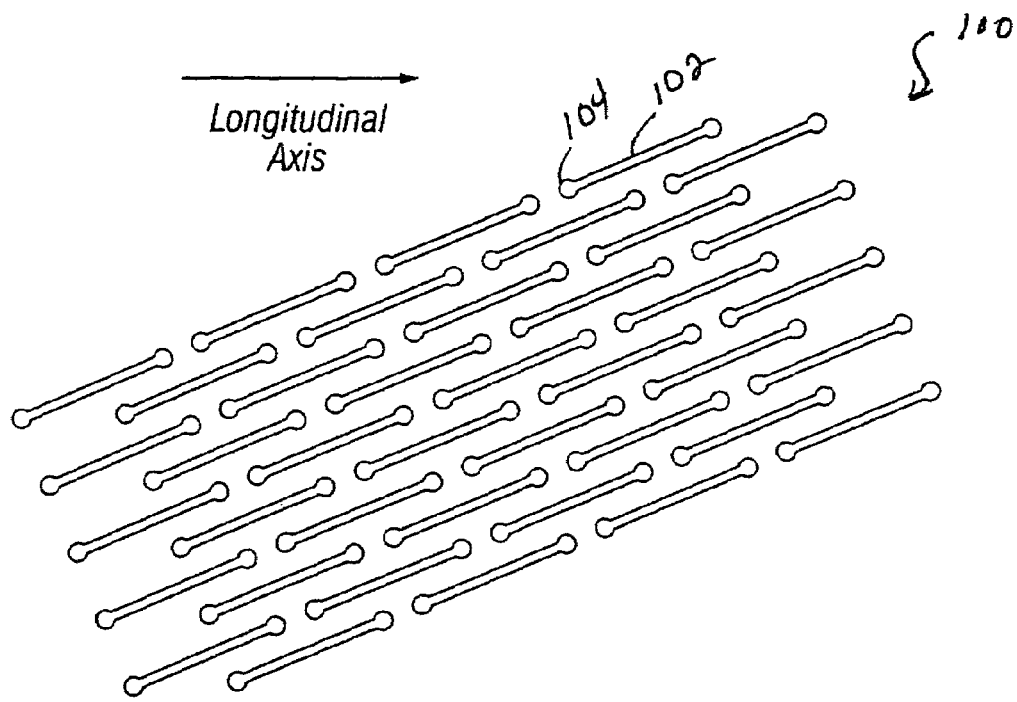
FIG. 10 is a plan view of a pattern of openings for a microporous metal thin film covering of an alternative embodiment of the present invention.

Opening pattern 100 illustrated in FIG. 10 is identical to that depicted in FIG. 9, except that the longitudinal axis of the plurality of openings 102 is angularly displaced from the longitudinal axis of the microporous metal thin film covering, but is neither parallel nor perpendicular thereto.

Figure 11:
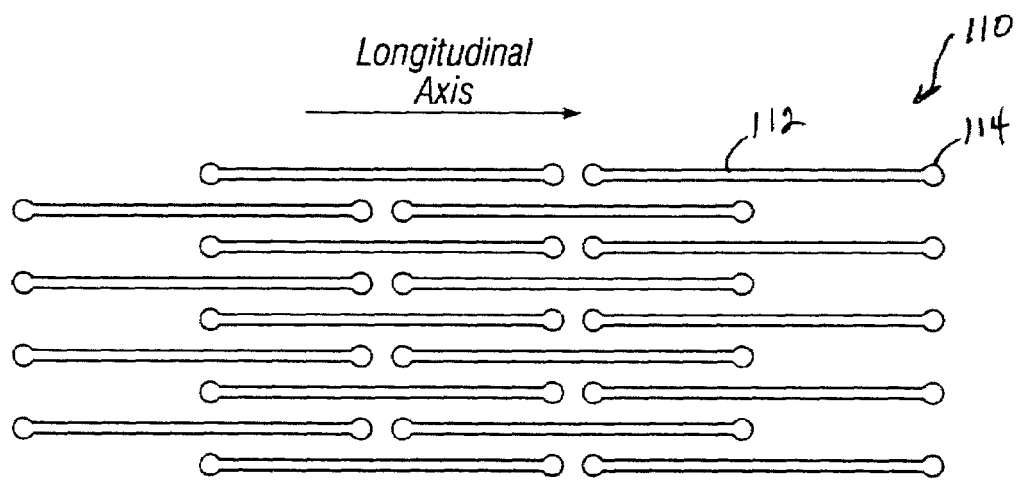
FIG. 11 is a plan view of a pattern of openings for a microporous metal thin film covering of an alternative embodiment of the present invention.

Opening pattern 110 illustrated in FIG. 11 is identical to that depicted in FIGS. 9 and 10, except that each of the plurality of openings 112 having filleted openings 114 have a longitudinal axis oriented parallel to the longitudinal axis of the microporous metal thin film covering such that radially expansive properties are imparted to the metal thin film covering.

Figure 12:
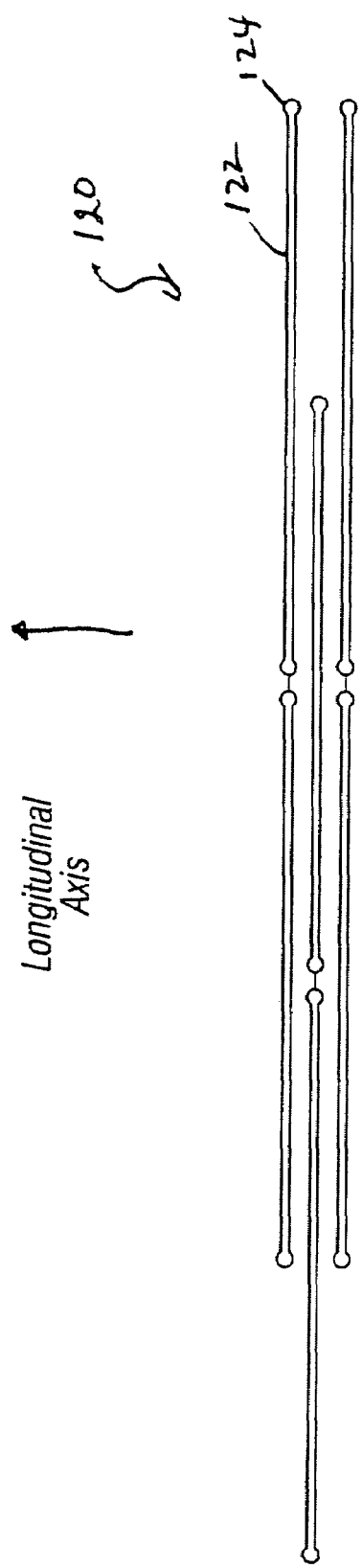
FIG. 12 is a plan view of a pattern of openings for a microporous metal thin film covering of an alternative embodiment of the present invention.
Figure 14:
FIG. 14 is a plan view of a pattern of openings for a microporous metal thin film covering of an alternative embodiment of the present invention.
Figure 13:
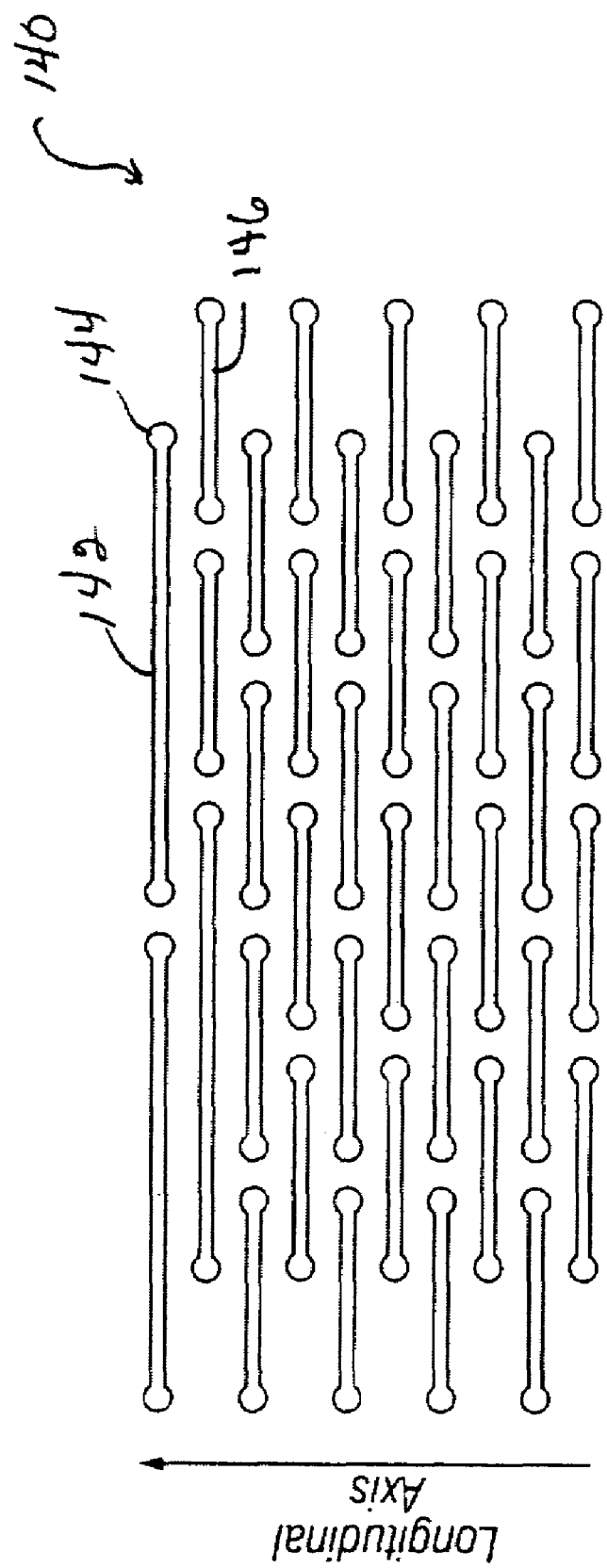
FIG. 13 is a plan view of a pattern of openings for a microporous metal thin film covering of an alternative embodiment of the present invention.

In FIGS. 12 and 13, opening patterns 120 and 130 are similar to that depicted in FIG. 9, except that the dimension of each of the longitudinal slots 122, 132 having filleted openings 124, 134 at opposing ends thereof have a longer dimension in the longitudinal axis of the opening 122, 132. In FIG. 12, the longitudinal axis of the longitudinal slots 122 are perpendicular to the longitudinal axis of the microporous metal thin film to impart longitudinally expansive properties to the metal thin film covering, while in FIG. 13, the longitudinal axis of the longitudinal slots 132 are parallel to the longitudinal axis of the metal thin film covering to impart radially expansive properties to the metal thin film covering.

The opening pattern 140 depicted in FIG. 13 is similar to that depicted in FIG. 9, except that there are a plurality of different length dimensions of the longitudinal slots 142 and 146, each having filleted openings 144 at opposing ends thereof and oriented perpendicular to the longitudinal axis of the microporous metal thin film covering.

Figure 15:
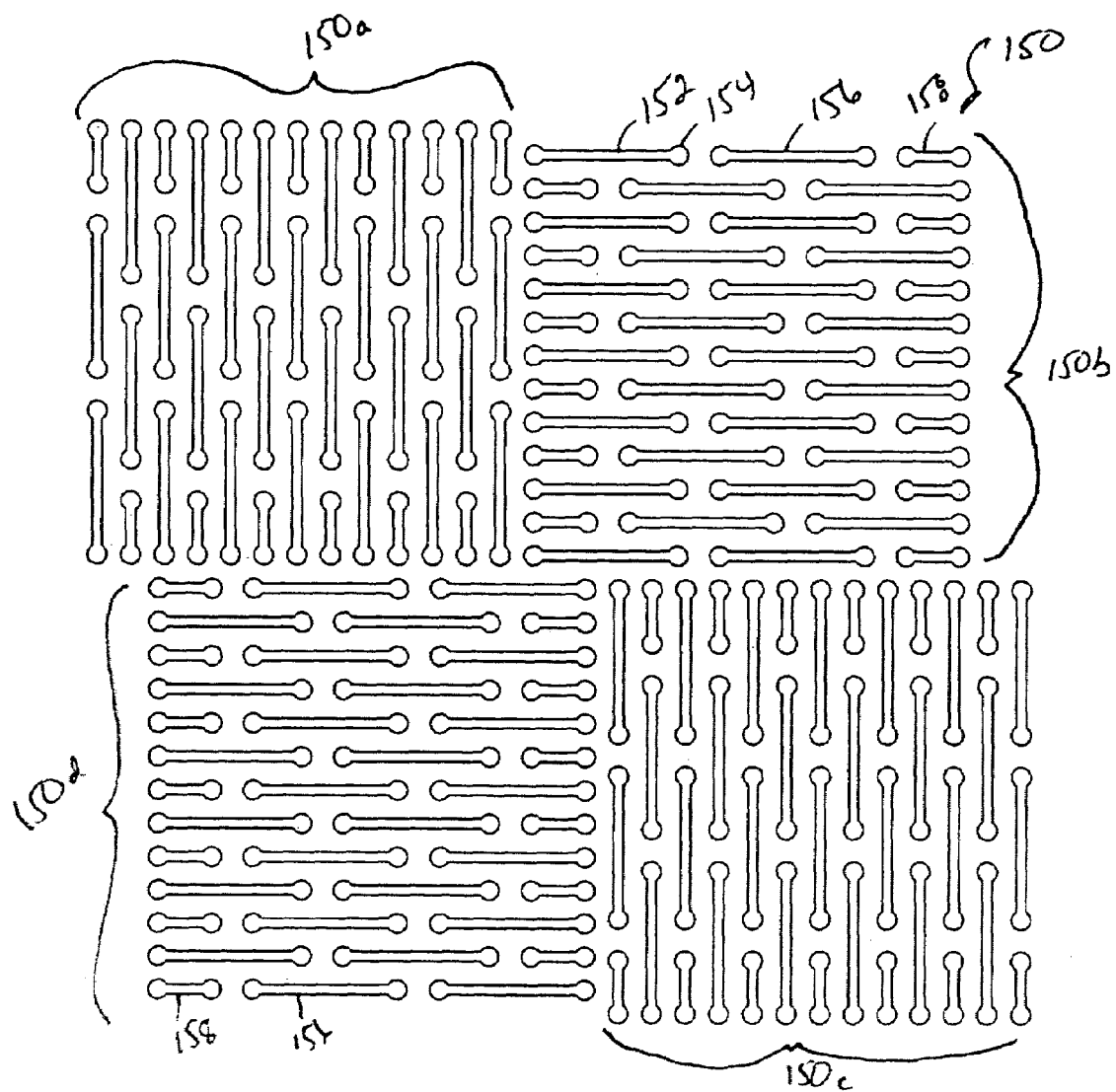
FIG. 15 is a plan view of a pattern of openings for a microporous metal thin film covering of an alternative embodiment of the present invention.

FIG. 15 illustrates yet another alternative opening pattern 150 in which there are a plurality of different length dimensions of the longitudinal slots 152, 156, 158, all having filleted openings 154 at ends thereof. Additionally, the opening pattern 150 is characterized by having groups of longitudinal slots 152, 156, 158 arrayed parallel to the longitudinal axis of the metal thin film covering and groups of longitudinal slots 152, 156 and 158 arrayed perpendicular to the longitudinal axis of the metal thin film covering such that a first group 150*a* and 150*c* have a common longitudinal axis, while second group 150*b* and fourth group 150*d* have a common longitudinal axis that is also perpendicular to the longitudinal axis of the first 150*a* and third 150*c* groups. Within each group adjacent rows of longitudinal slot openings are staggered on one-half length offsets. In this manner, the microporous metal thin film covering has a generally checkerboard pattern of opening groups and will exhibit both radial and longitudinal expansibility.

Figure 16:
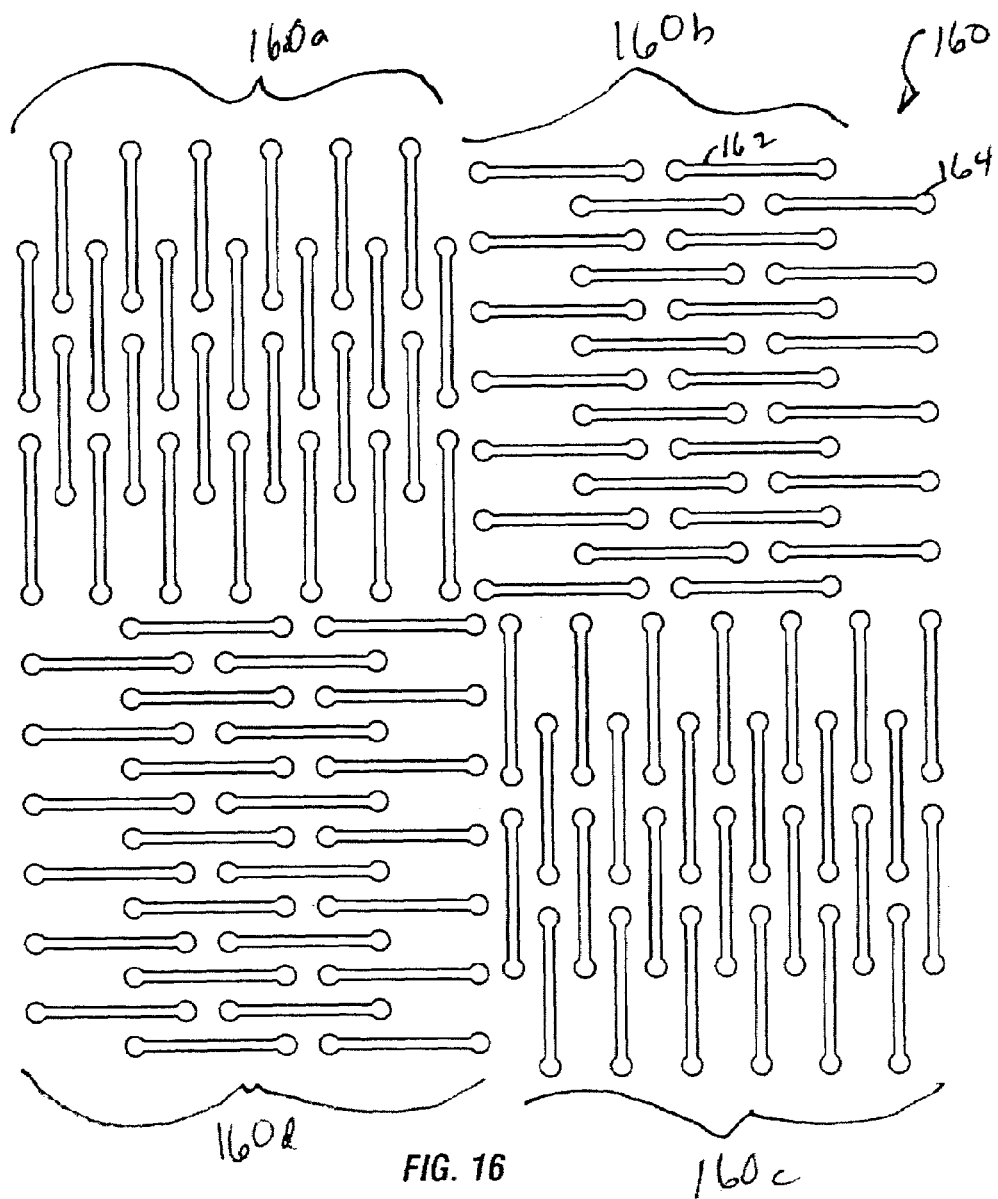
FIG. 16 is a plan view of a pattern of openings for a microporous metal thin film covering of an alternative embodiment of the present invention.

FIG. 16 is similar to FIG. 15, except that there is a common longitudinal dimension of each longitudinal slot 162, again having filleted openings 164 at opposing ends thereof. Like the pattern 150 illustrated in FIG. 15, opening pattern 160 is characterized by having groups of longitudinal slots 162 arrayed parallel to the longitudinal axis of the metal thin film covering and groups of longitudinal slots 162 arrayed perpendicular to the longitudinal axis of the metal thin film covering such that a first group 160*a* and 160*c* have a common longitudinal axis, while second group 160*b* and fourth group 160*d* have a common longitudinal axis that is also perpendicular to the longitudinal axis of the first 160*a* and third 160*c* groups.

In this manner, the microporous metal thin film covering has a generally checkerboard pattern of opening groups and will exhibit both radial and longitudinal expansibility.

Figure 17:
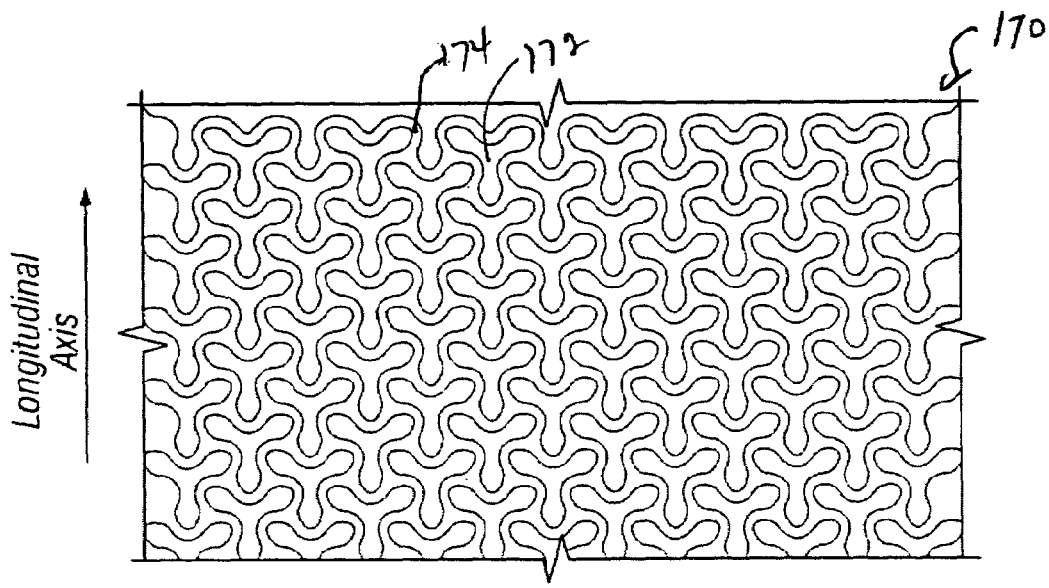
FIG. 17 is a plan view of a pattern of openings for a microporous metal thin film covering of an alternative embodiment of the present invention.
Figure 25:
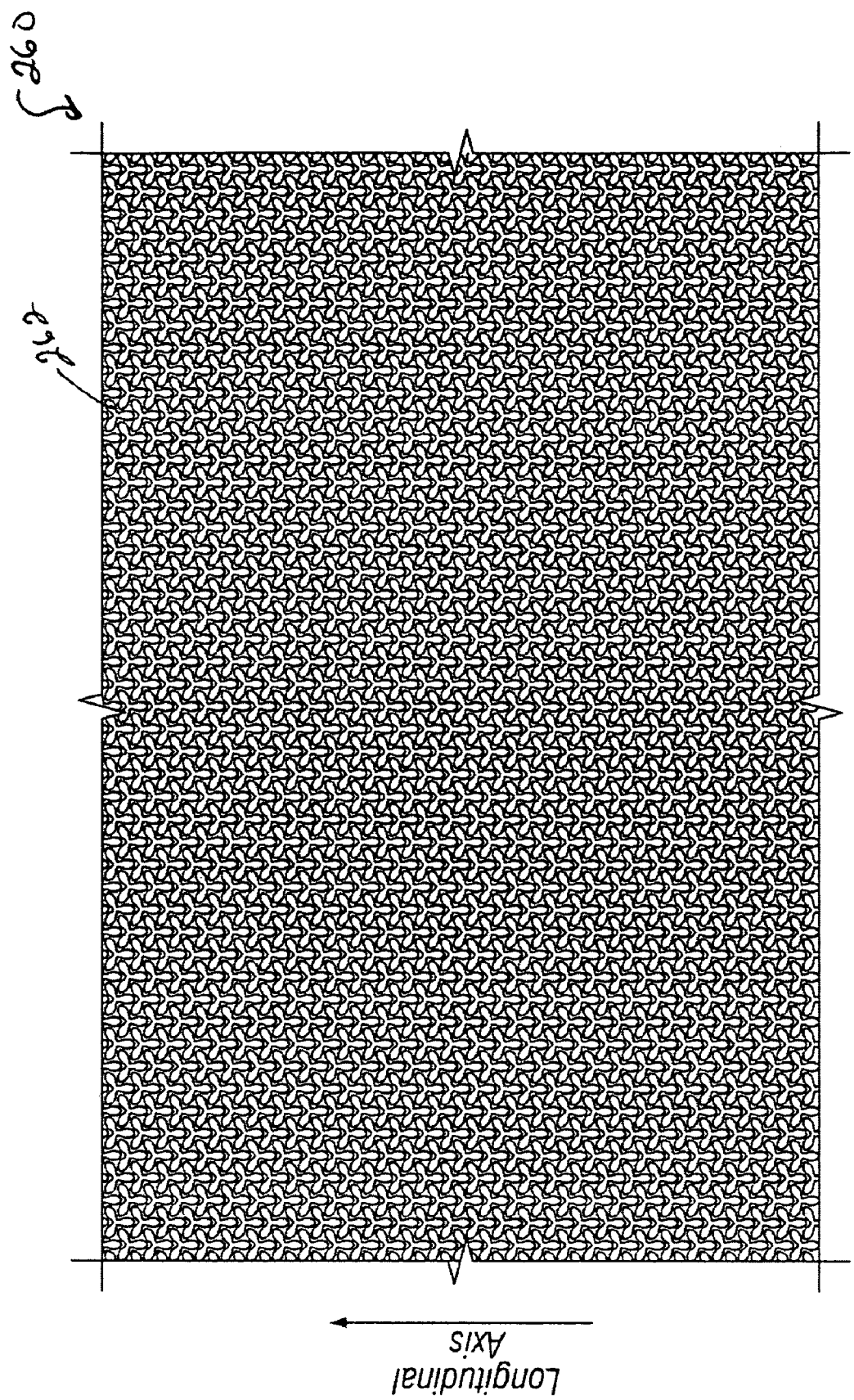
FIG. 25 is a plan view of a pattern of openings for a microporous metal thin film covering of an alternative embodiment of the present invention.

FIG. 17 illustrates still another alternate geometry 170 of the microporous openings 172 in the metal thin film covering member 174. In accordance with geometry 170, each of the microporous openings 172 has a generally tri-leafed, Y-shaped opening with having each of the tri-leafs offset by approximately 120 degrees on center. The plurality of microporous openings 172 are arrayed in such a manner as to minimize spacing between openings 172 and have the metal thin film covering member 174 traverse a highly circuitous path between the plurality of microporous openings 172. This tri-leafed, Y-shaped opening shape of the microporous openings 172 will lend both radial and longitudinal expansion characteristics to the metal thin film covering member 172, and unlike the longitudinal slot openings of other embodiments previously described, also permits expansion along an axis intermediate to the radial and longitudinal axis of the metal thin film covering member 174. Upon expansion, each of the tri-leafed, Y-shaped openings expand to generally circular opening shapes. FIG. 25 depicts a plan view of a graft material 260 having a plurality of tri-leafed Y-shaped openings 262 that is similar to the geometry 170, but in a larger view.

Figure 18:
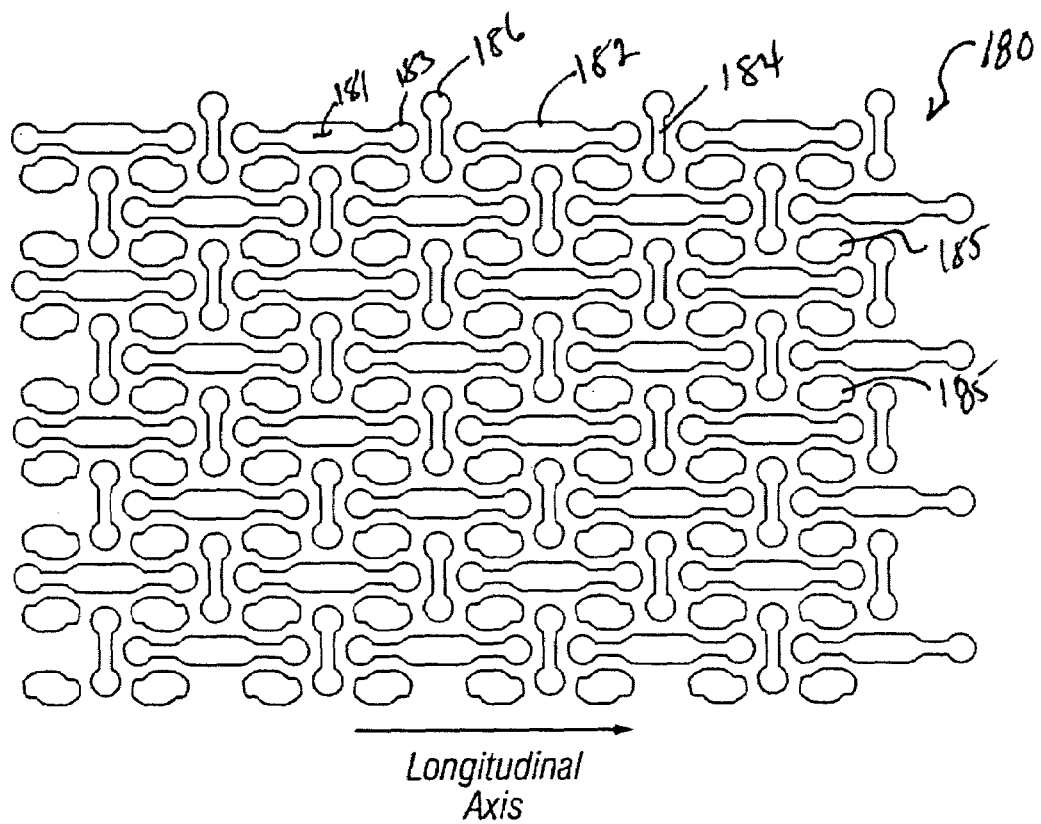
FIG. 18 is a plan view of a pattern of openings for a microporous metal thin film covering of an alternative embodiment of the present invention.
Figure 19:
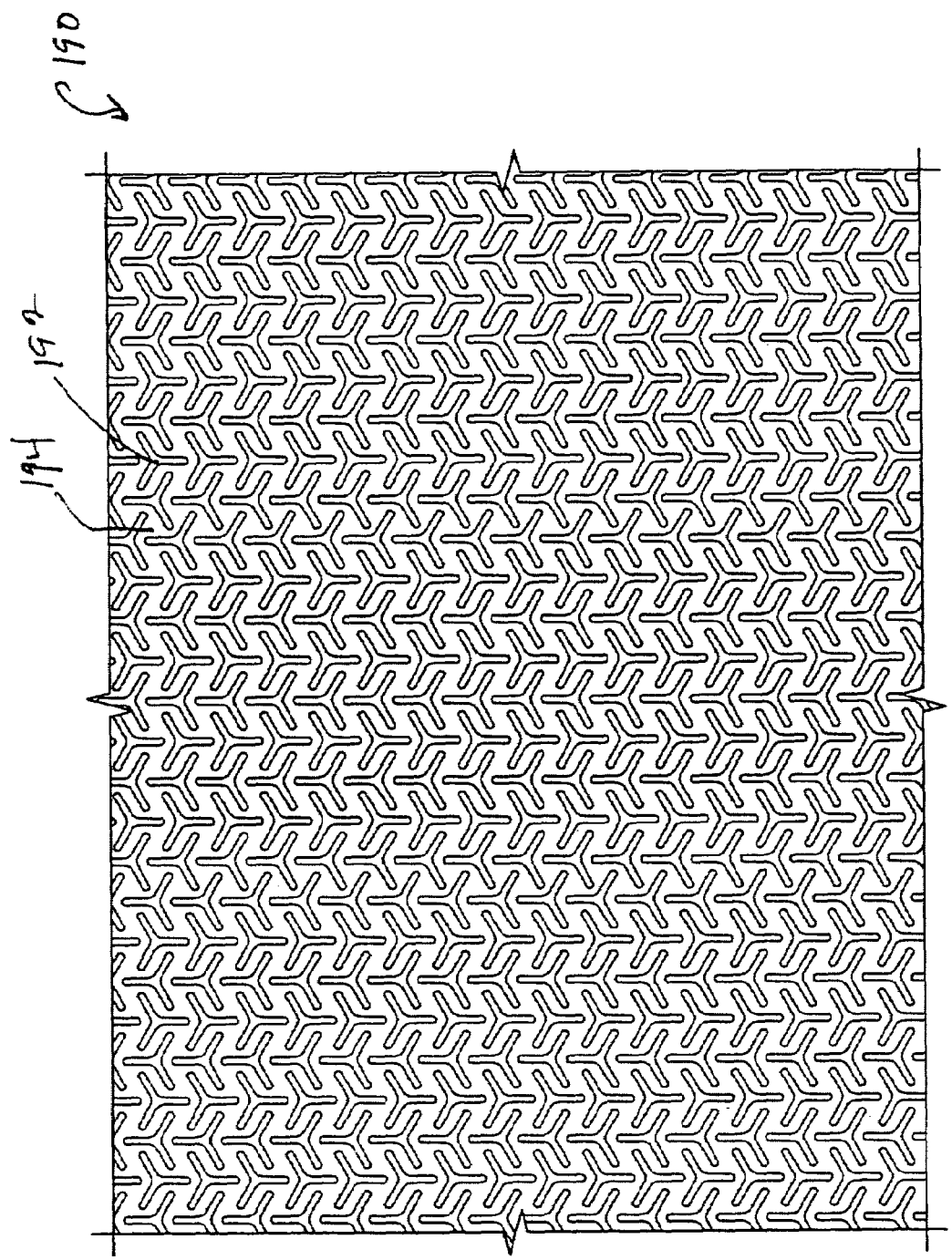
FIG. 19 is a plan view of a pattern of openings for a microporous metal thin film covering of an alternative embodiment of the present invention.

FIG. 18 depicts another alternate geometry 180 for the inventive microporous metal thin film covering. In accordance with geometry 180, the plurality of microporous openings have several different opening shapes. A first opening comprises a plurality of elongate slot openings 182 having an enlarged intermediate section 181 and filleted openings 183 at opposing ends of each elongate slot opening 182. The elongate slot openings 182 are arrayed such that their longitudinal axis is parallel to the longitudinal axis of the metal thin film covering member. A second opening comprises a slot opening 184 having a longitudinal axis shorter than the first opening 182, has a uniform dimensioned intermediate section and filleted openings 183 at opposing ends thereof. Each of the second openings 184 has a longitudinal axis perpendicular to the longitudinal axis of the metal thin film covering member. Finally, a third opening 185 is provided with an enlarged generally S-shape, with its longitudinal axis arrayed generally parallel to the longitudinal axis of the metal thin film covering member. In accordance with geometry 180, the plurality of first openings 182 are arrayed in adjacent offset rows along the longitudinal axis of the metal thin film covering member. A second opening 184 is positioned between pairs of longitudinally adjacent first openings 182 and positioned to form circumferentially oriented rows perpendicular to the longitudinal axis of the metal thin film covering member. The plurality of third openings 185 are positioned in longitudinally expending rows intermediate circumferentially adjacent longitudinal rows of the first opening 182 and between adjacent circumferential rows of second opening 184.

Figure 26:
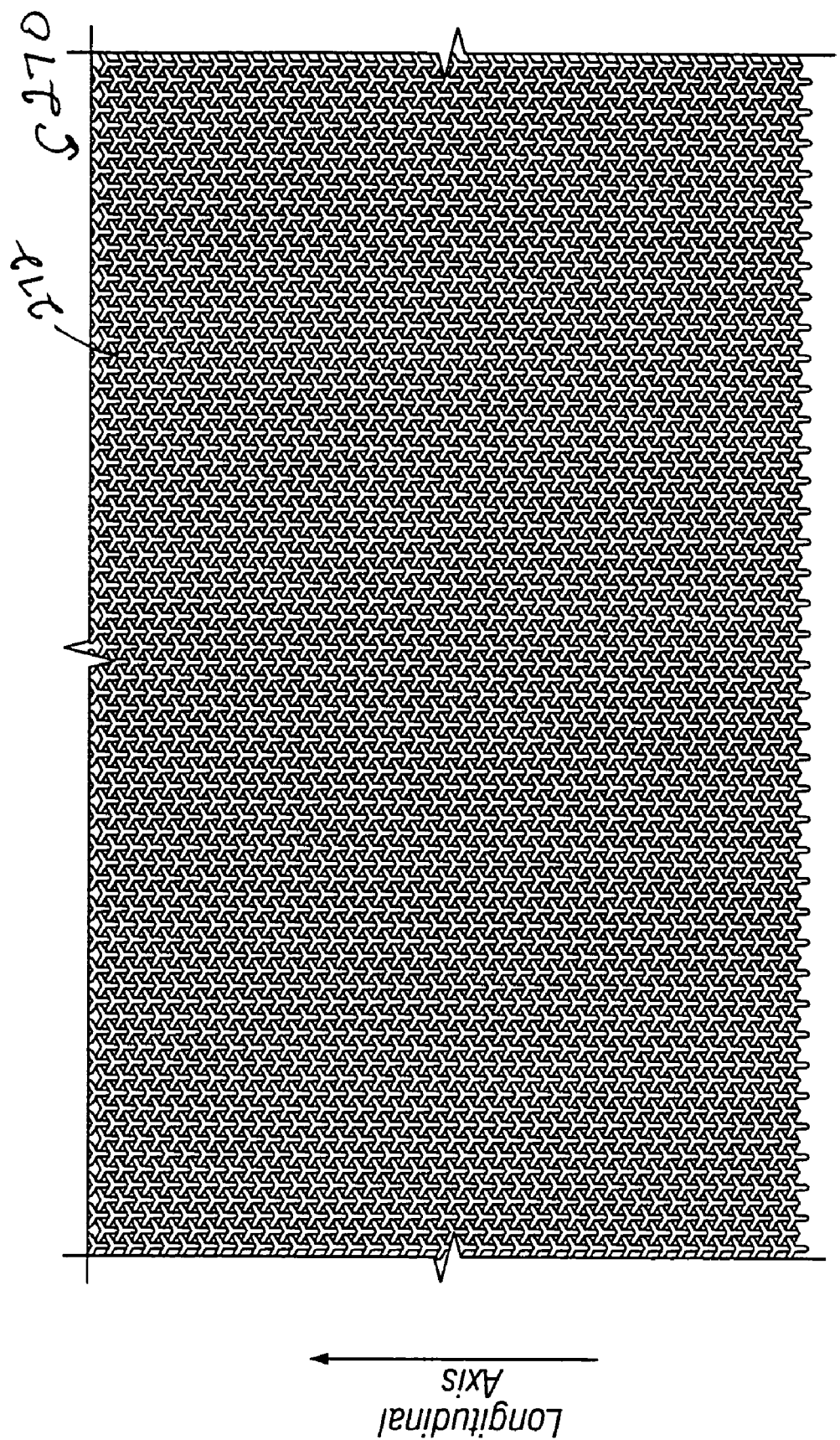
FIG. 26 is a plan view of a pattern of openings for a microporous metal thin film covering of an alternative embodiment of the present invention.

In accordance with another preferred embodiment, geometry 190 is provided. In accordance with geometry 190, a plurality of tri-legged, generally Y-shaped openings 190 are provided in the metal thin film covering material 194, with the openings 190 being oriented in an offset array along either the longitudinal or circumferential axis of the metal thin film covering material 194. Like the embodiment illustrated in FIG. 17, openings 190 permit expansion of the metal thin film covering material 194 along virtually any axis of the material 194, thereby imparting a high degree of compliance. Upon expansion, each of the openings 190 will assume a generally circular shape. FIG. 26 depicts a plan view of a graft material 270 having a plurality of tri-leafed Y-shaped openings 272 that is similar to the geometry 190, but in a larger view.

Figure 20:
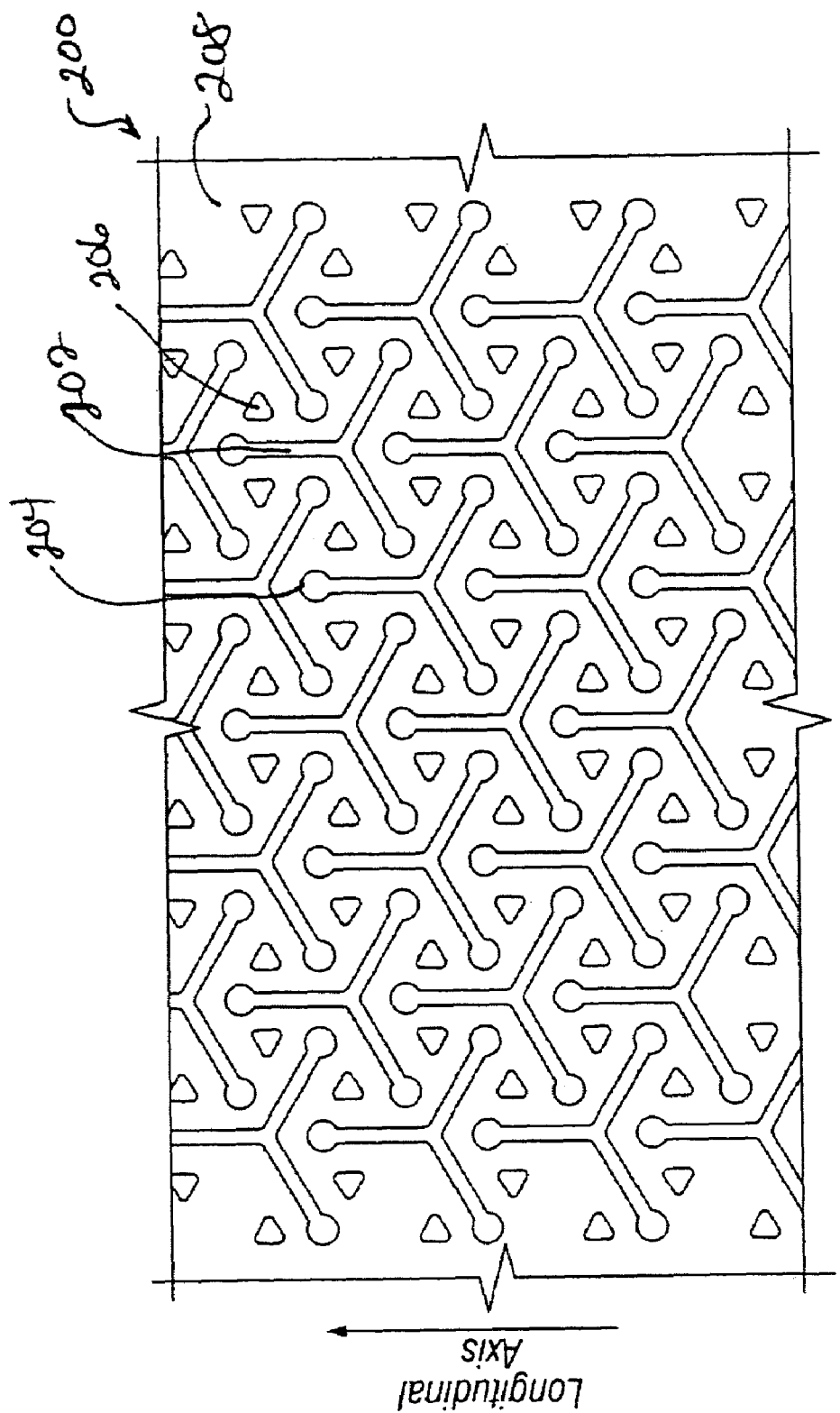
FIG. 20 is a plan view of a pattern of openings for a microporous metal thin film covering of an alternative embodiment of the present invention.

FIG. 20 illustrates still another embodiment of a pattern 200 of microporous openings. Like geometry 190, there are provided a plurality of tri-leafed, Y-shaped openings 202 arrayed along both the longitudinal circumferential axes of the metal thin film covering material 208. However, in pattern 200, each of the tri-leafed legs of the openings 202 have generally circular fillets 204 at ends thereof and a pair of generally triangular shaped openings 206 on opposing lateral aspects of each of the tri-leafed legs. Like geometry 190, pattern 200 will exhibit compliance in virtually any axis of the metal thin film covering material 208.

Figure 21:
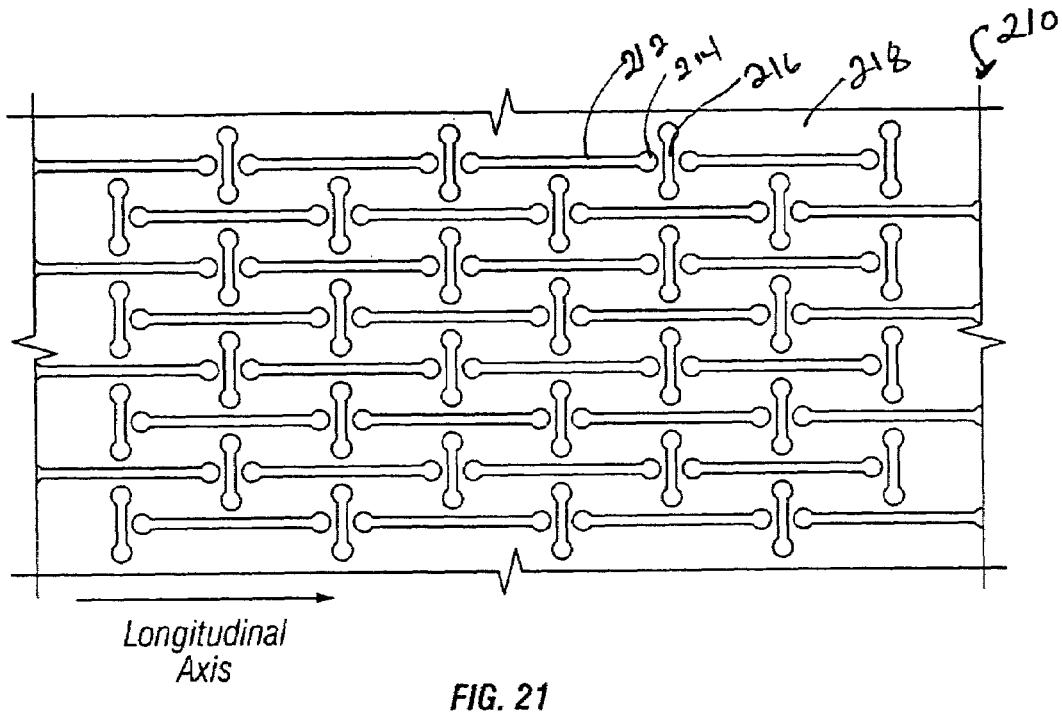
FIG. 21 is a plan view of a pattern of openings for a microporous metal thin film covering of an alternative embodiment of the present invention.
Figure 22:
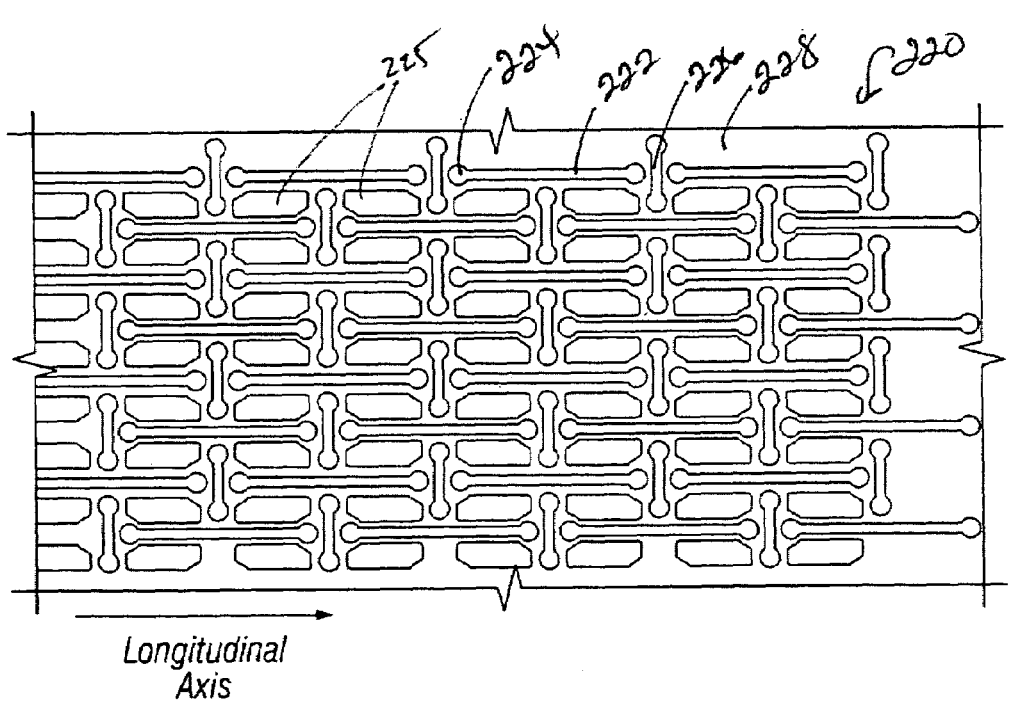
FIG. 22 is a plan view of a pattern of openings for a microporous metal thin film covering of an alternative embodiment of the present invention.

FIGS. 21 and 22 represent alternate related geometries 210 and 220, respectively. Common to both geometries 210 and 220 are a plurality of elongate longitudinally extending slots 212, 222 having generally circular fillets 214, 224 at opposing ends thereof, and arrayed in adjacent, offset rows extending along the longitudinal axis of the metal thin film covering member. A plurality of relative shorter circumferentially oriented slots 216, 226, also having generally circular fillets at opposing ends thereof, are arrayed adjacent, offset rows extending along the circumferential axis of the metal thin film covering member. Each of the plurality of relatively shorter slots 216, 226 is positioned intermediate longitudinally adjacent pairs of elongate longitudinally extending slots 212 and 222. The difference between geometry 210 and 220 is that in geometry 220 there are an additional plurality of generally trapezoidal fenestrations 225 in the metal thin film covering material 228 that are bounded by section of two circumferentially adjacent and offset elongate slots 222 and two longitudinally adjacent and offset relatively shorter slots 226. Both geometries 210 and 220 will lend compliance in both the radial and the longitudinal axis of the metal thin film material.

Figure 23:
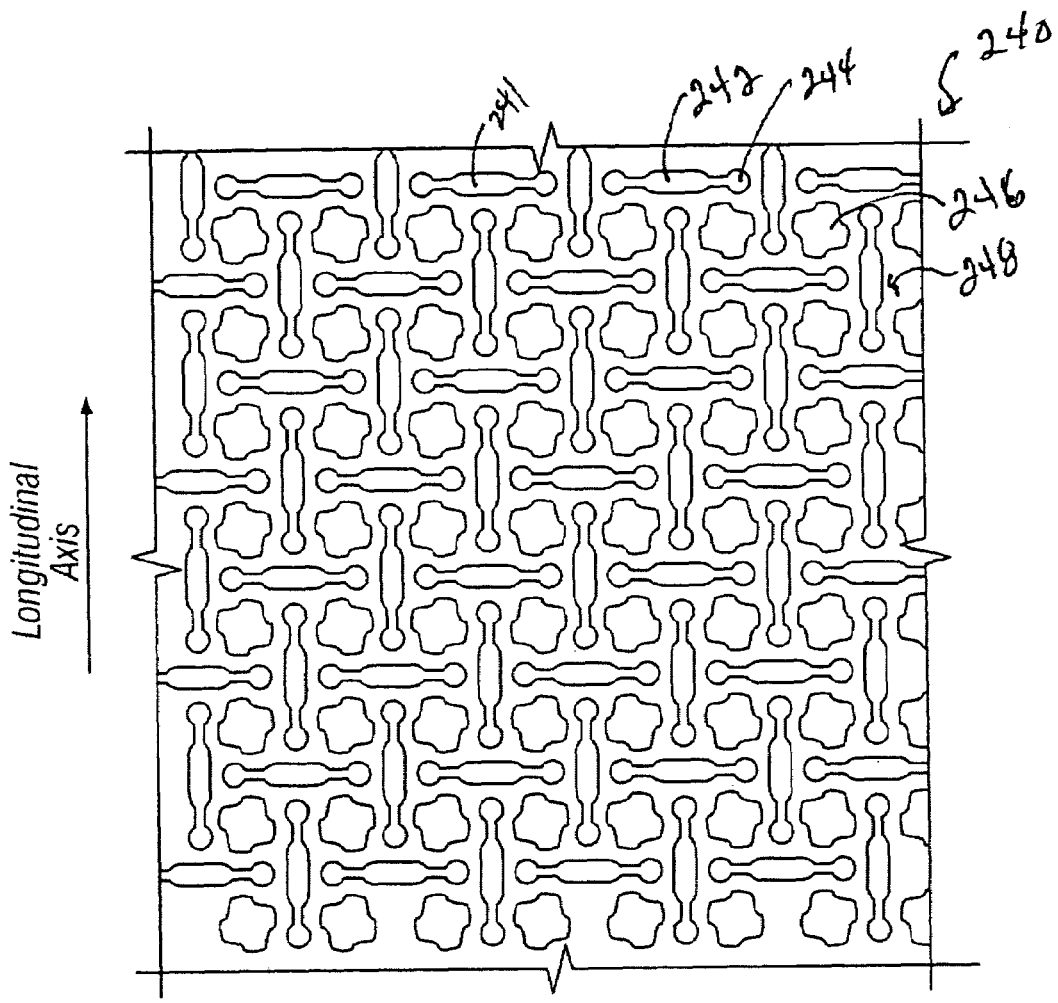
FIG. 23 is a plan view of a pattern of openings for a microporous metal thin film covering of an alternative embodiment of the present invention.

FIG. 23 illustrates yet another geometry 240 for the openings in the metal thin film covering material 248. Geometry 240 displays a high degree of similarity to geometry 180 illustrated in FIG. 18, except that all of the longitudinal slot openings 242 have an enlarged intermediate section 241, and are arrayed in both the longitudinal axis and the circumferential axis of the metal thin film covering material 248, such that a single circumferentially oriented slot opening 242 is positioned intermediate adjacent pairs of longitudinally oriented slot openings 242. A plurality of generally cruciform fenestrations 246 are also provided in the metal thin film covering material 248 and are bounded by a pair of longitudinally oriented slot openings 242 and a pair of circumferentially oriented slot openings 242. Geometry 240 will exhibit compliance in both the longitudinal and circumferential axes of the metal thin film material 248.

Figure 24:
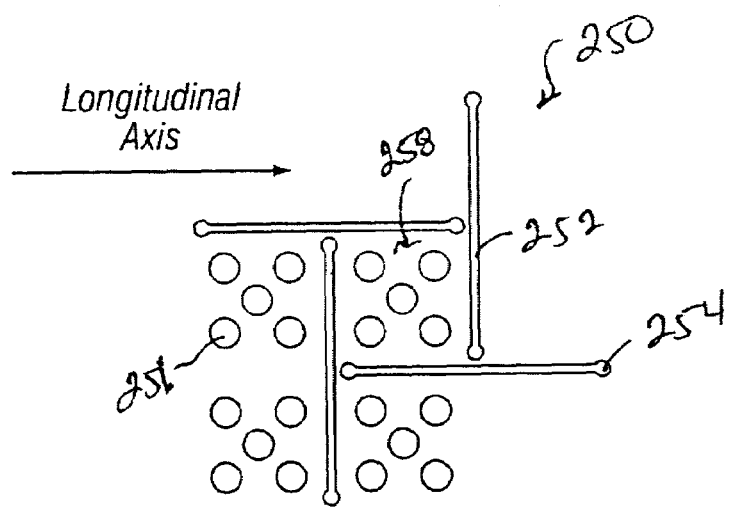
FIG. 24 is a plan view of a pattern of openings for a microporous metal thin film covering of an alternative embodiment of the present invention.

Finally, FIG. 24 depicts another geometry 250 of the openings in a metal thin film material. Geometry 250 includes a plurality of circumferentially oriented elongate slots 252 and a plurality of longitudinally oriented elongate slots 254 oriented generally perpendicular with respect to one another. A plurality of generally circular openings 256 pass through the metal thin film material 258 in an area bounded by a pair of circumferentially extending elongate slots 252 and a pair of circumferentially extending elongate slots 254. Geometry 250 will also exhibit compliance in both the longitudinal and circumferential axes of the metal thin film material 258.

FIGS. 27-40 illustrate different geometries of structural support elements 300, 310, 320, 330, 340, 350, 360, 370, 380, 390, 400, 420, 430, 440, and 450 of alternative embodiments of the present invention. The various structural support elements exhibit the ability to radially expand and support a microporous metal thin film covering and also have the flexibility to maneuver through anatomic passageways including the vascular system. In addition to the depicted geometries, other known geometries of stents are contemplated for alternative embodiments of the present invention provided that the stent geometry has the necessary ability to radially expand and support a microporous metal thin film covering and the required flexibility.

Figure 27:
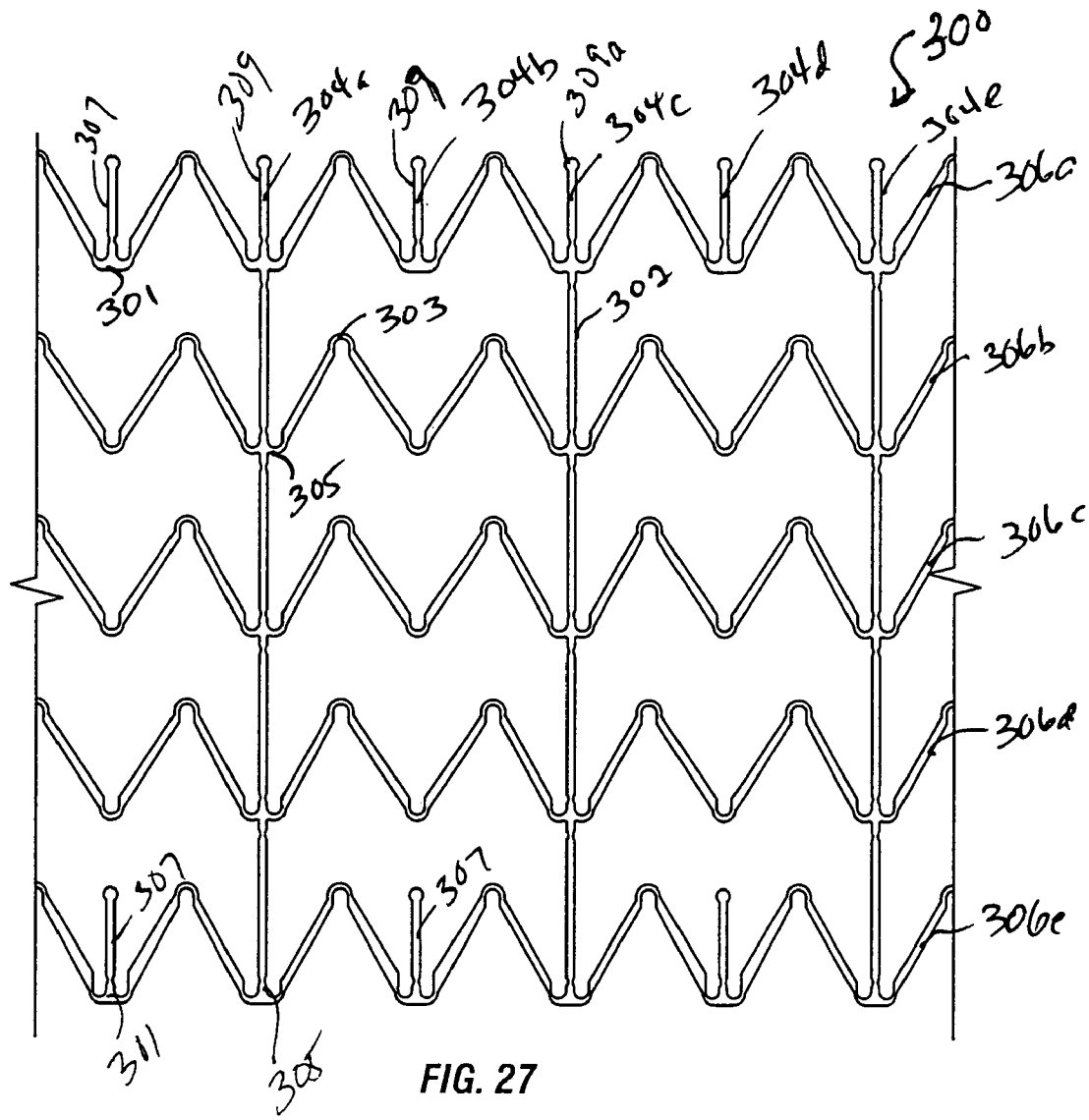
FIG. 27 is a plan view of a structural support element of an alternative embodiment of the implantable endoluminal graft while in an expanded diameter.

FIG. 27 depicts an embodiment of structural support element 300 in which there are provided a plurality of linear longitudinal elements 304a-304e, and a plurality of undulating circumferential elements 306a-306e, where each of the plurality of linear longitudinal elements 304a-304e form four point connections 305 with circumferential elements except for an end terminal circumferential element 304e which form three point connections 305. Notably, at least some of the linear longitudinal elements 304a-304e further have a terminal extension 309 that projects outward from at least one terminal end of the structural support element 300 and has a filleted rounded end 309a that serves as an attachment point for a metal thin film material (not shown). In accordance with a preferred embodiment, each of the undulating circumferential elements 306a-306e have a generally sinusoidal shape with a plurality of interconnected peaks 303 and valleys 301.

Figures 28A, 28B:
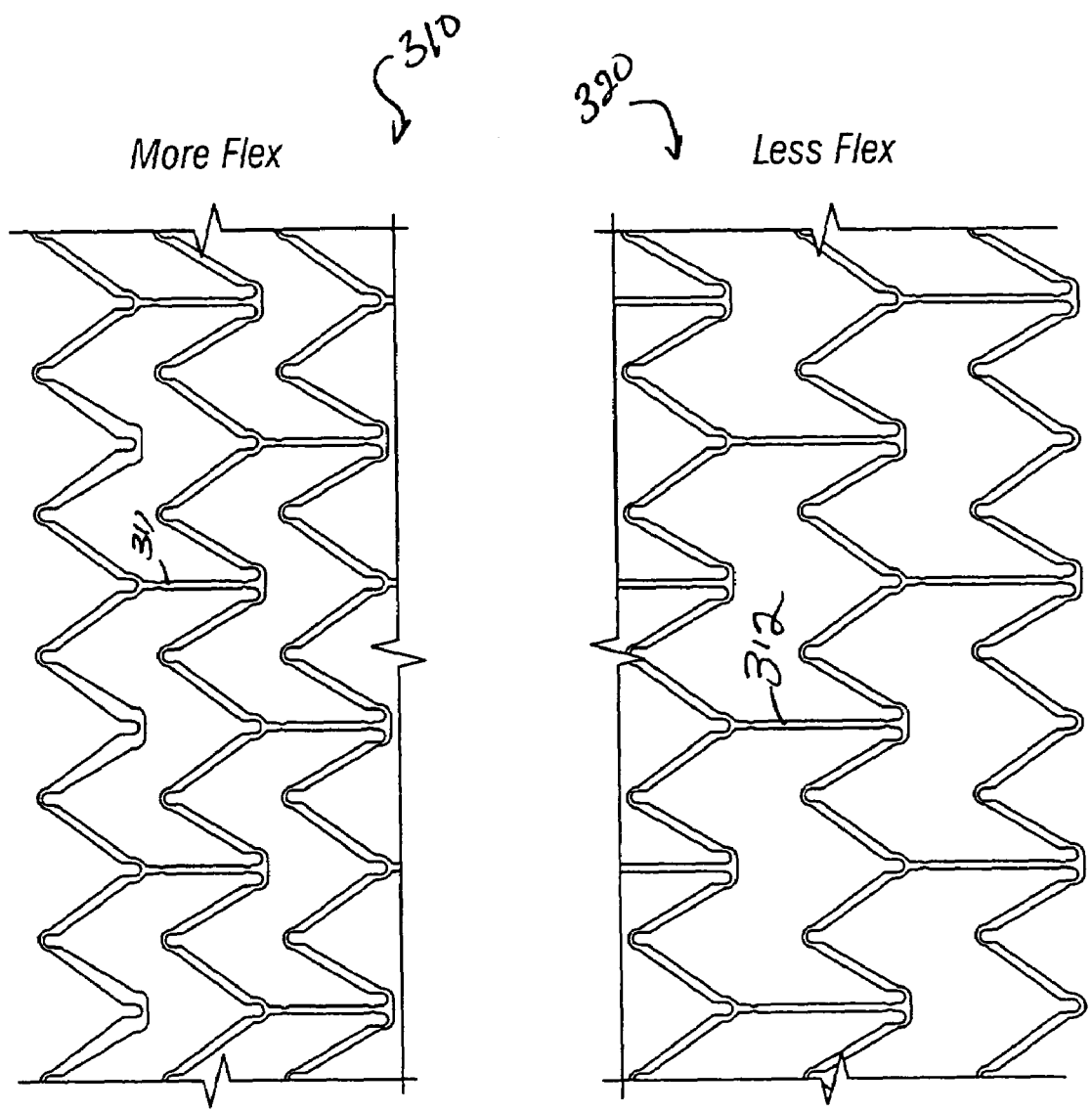
FIGS. 28a and 28b are plan views of a structural support element of an alternative embodiment of the implantable endoluminal graft while in an expanded diameter with short and long interconnecting members, respectively.
Figure 29:
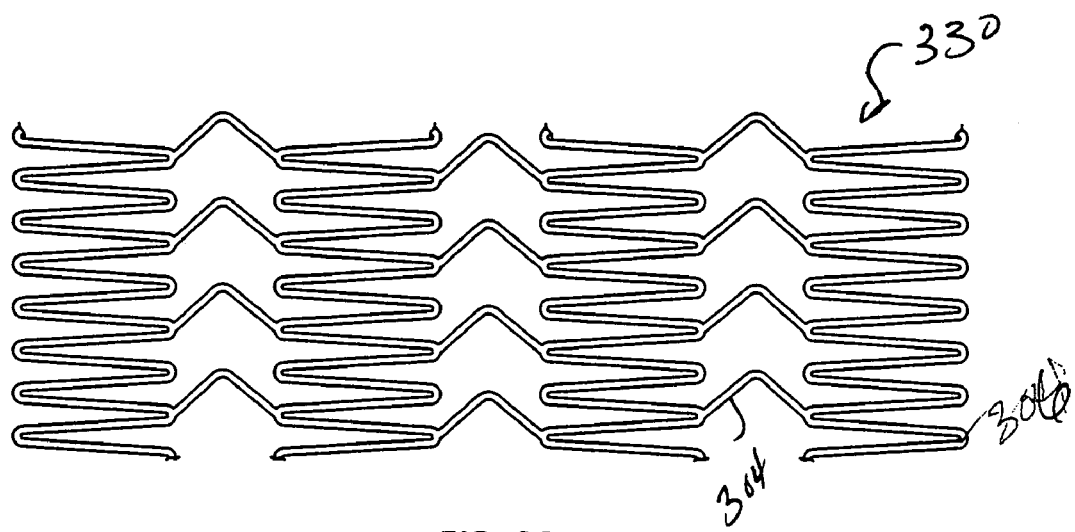
FIG. 29 is a plan view of a structural support element of an alternative embodiment of the implantable endoluminal graft.
Figure 30:
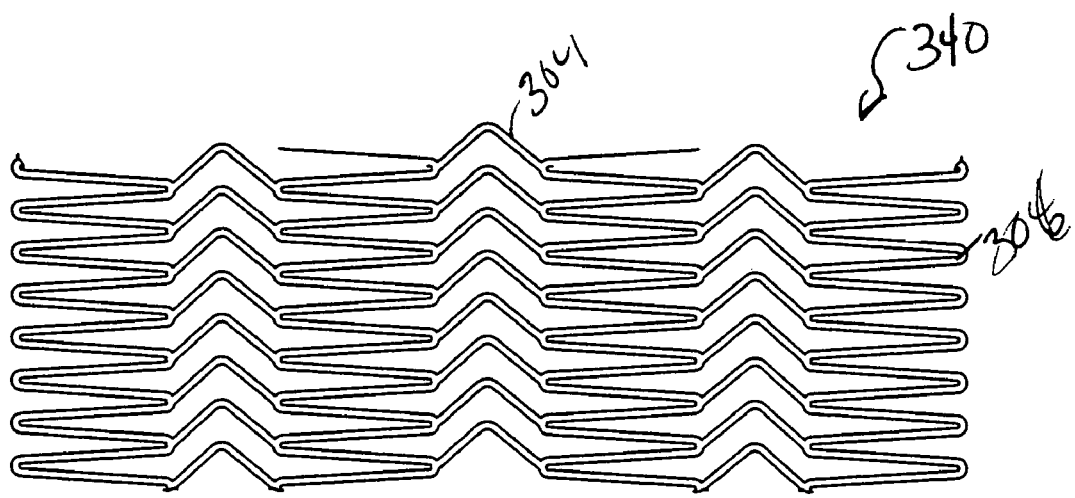
FIG. 30 is a plan view of a structural support element of an alternative embodiment of the implantable endoluminal graft.
Figure 31:
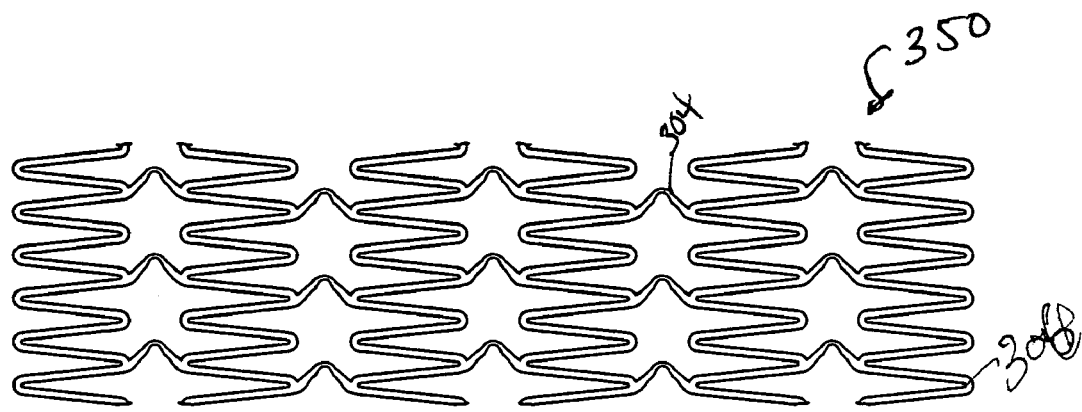
FIG. 31 is a plan view of a structural support element of an alternative embodiment of the implantable endoluminal graft.
Figure 32:
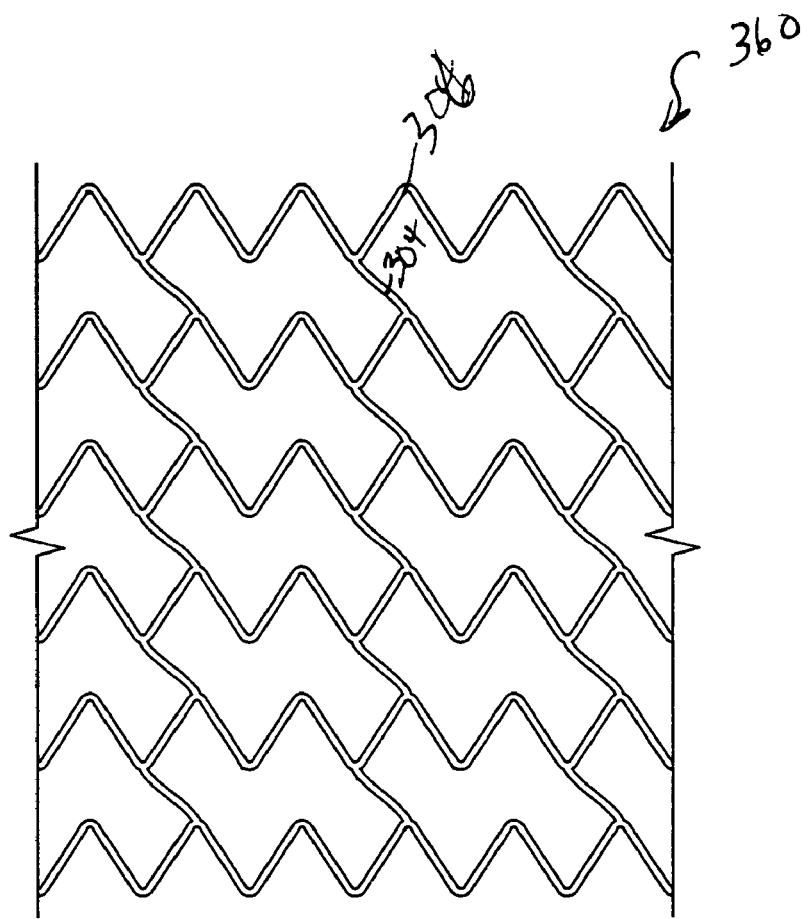
FIG. 32 is a plan view of a structural support element of an alternative embodiment of the implantable endoluminal graft.
Figure 33:
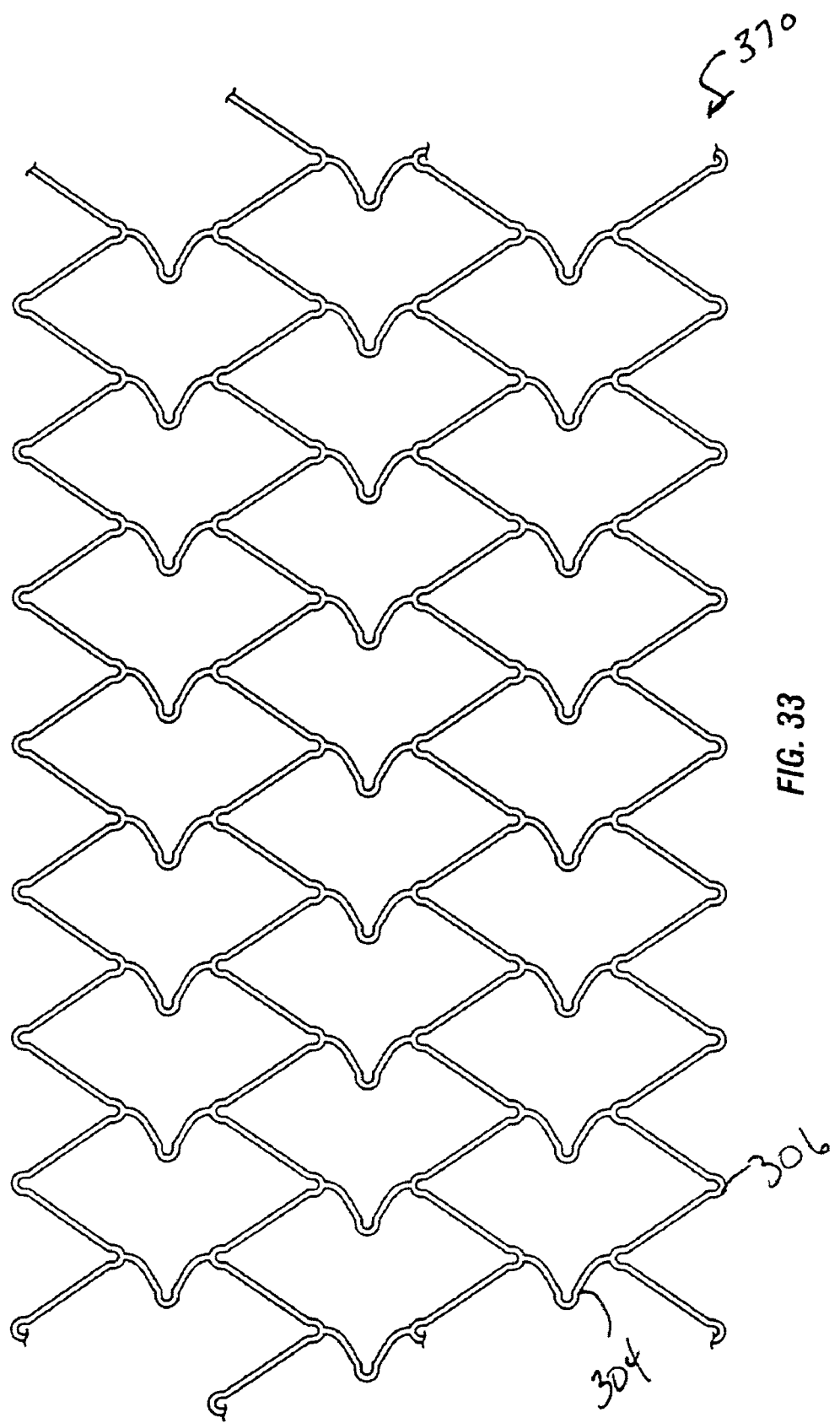
FIG. 33 is a plan view of a structural support element of an alternative embodiment of the implantable endoluminal graft.
Figure 34:
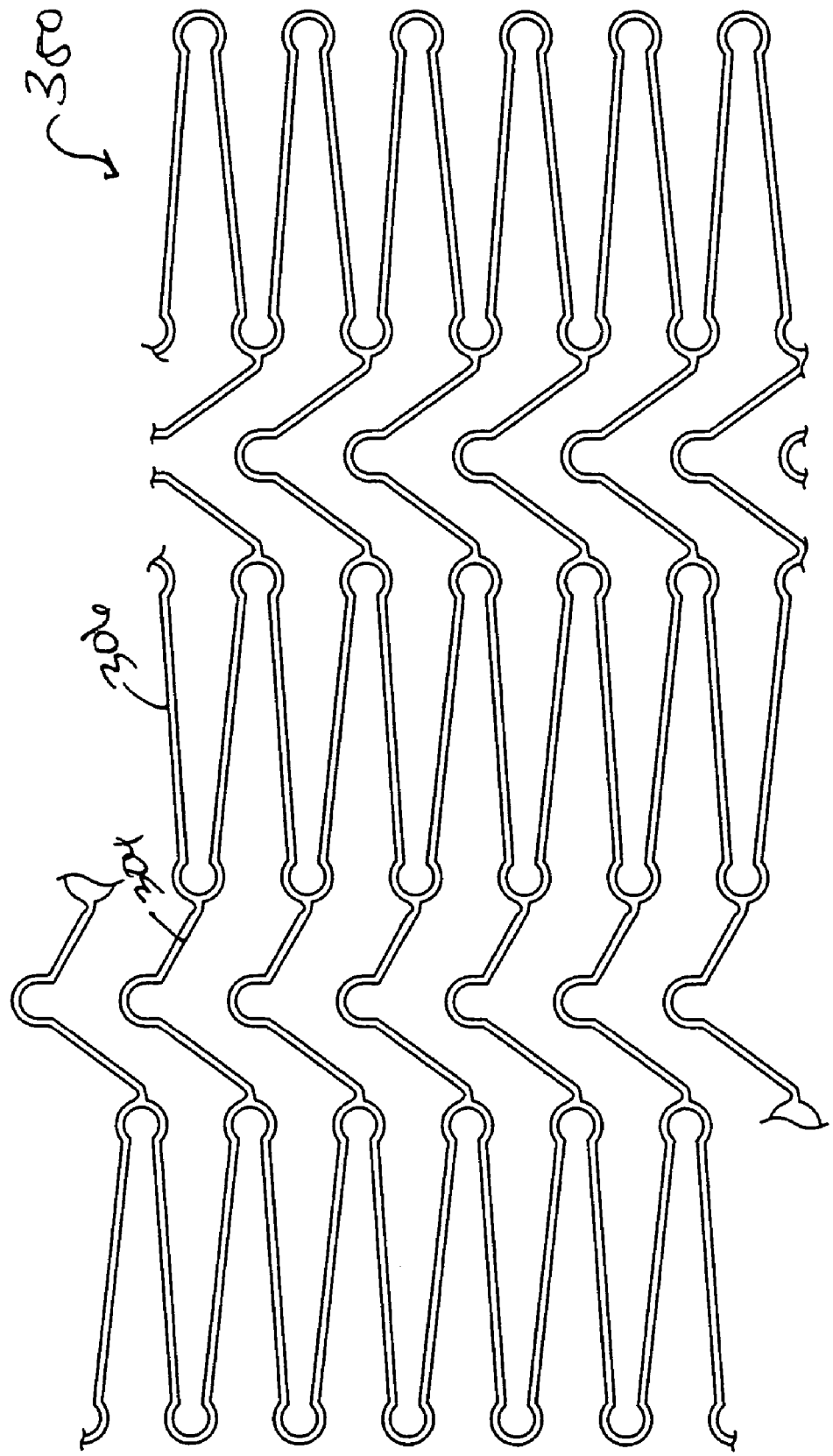
FIG. 34 is a plan view of a structural support element of an alternative embodiment of the implantable endoluminal graft.
Figure 35:
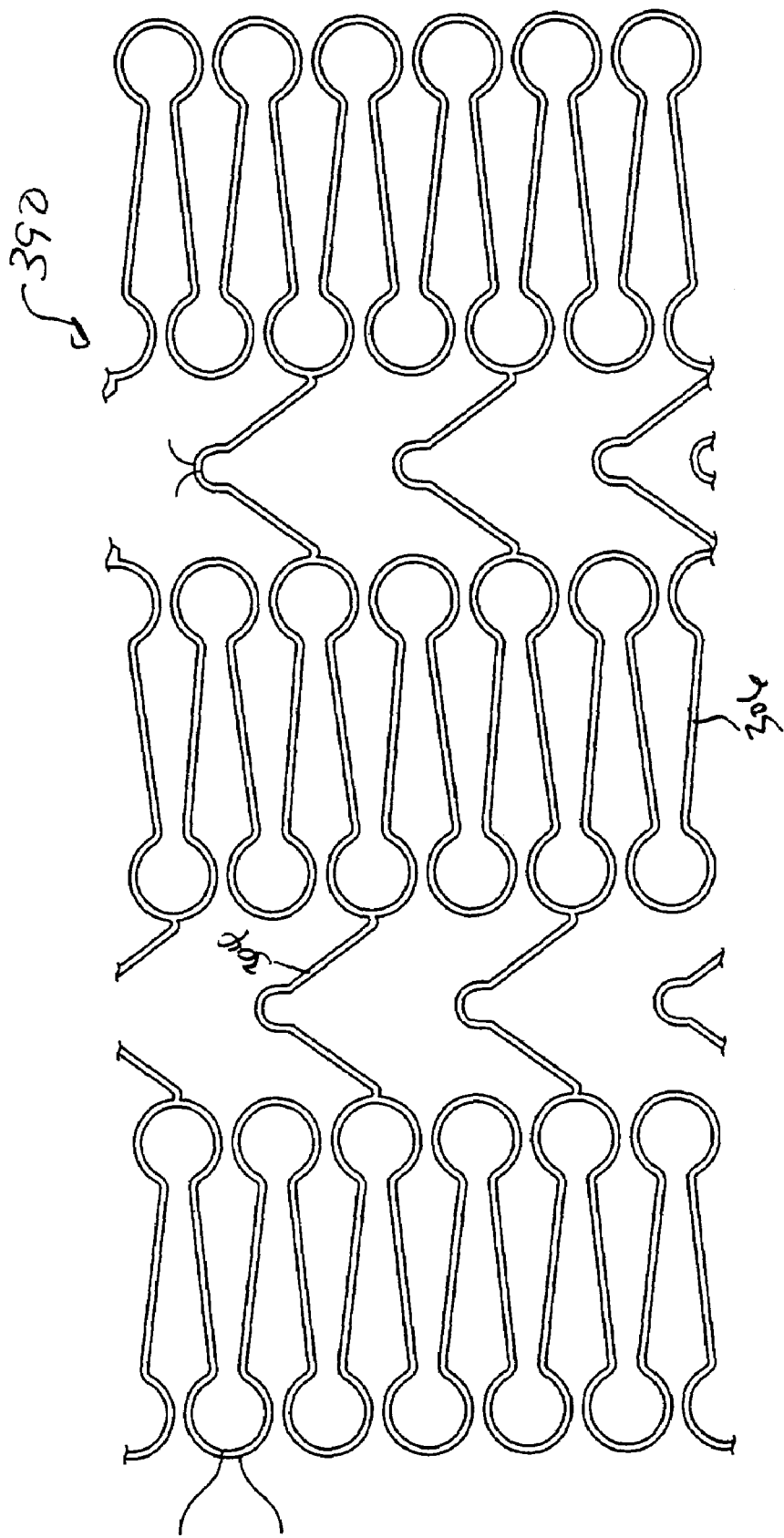
FIG. 35 is a plan view of a structural support element of an alternative embodiment of the implantable endoluminal graft.
Figure 36:
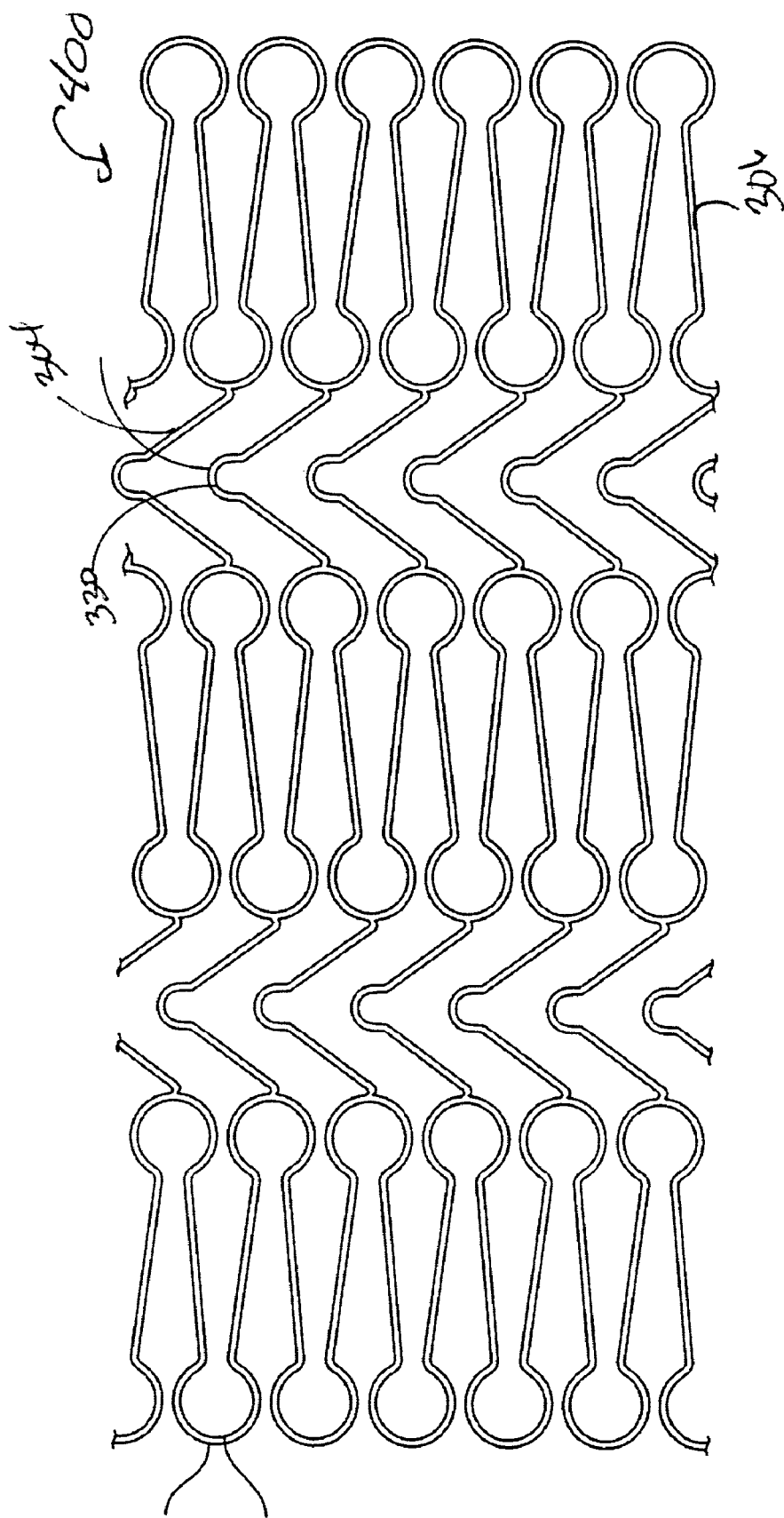
FIG. 36 is a plan view of a structural support element of an alternative embodiment of the implantable endoluminal graft.
Figure 37:
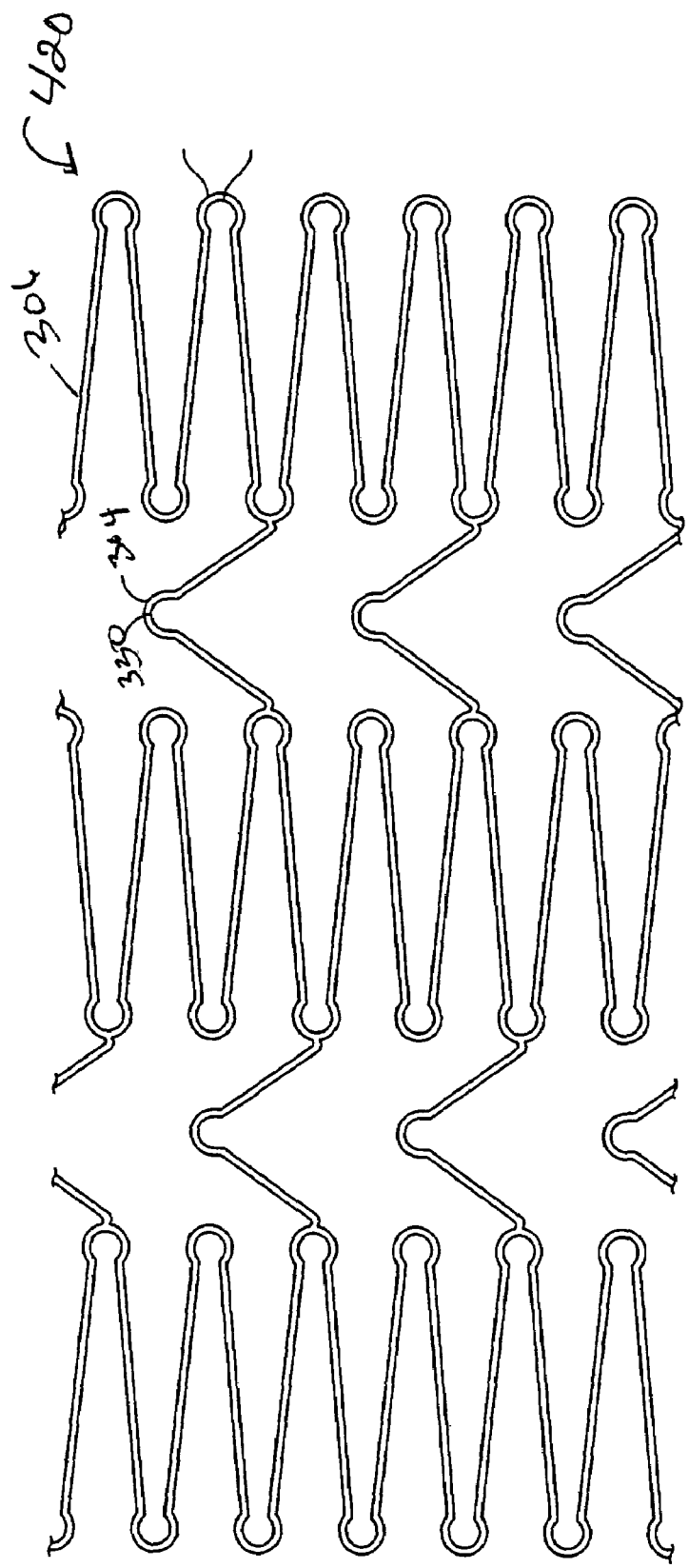
FIG. 37 is a plan view of a structural support element of an alternative embodiment of the implantable endoluminal graft.
Figure 38:
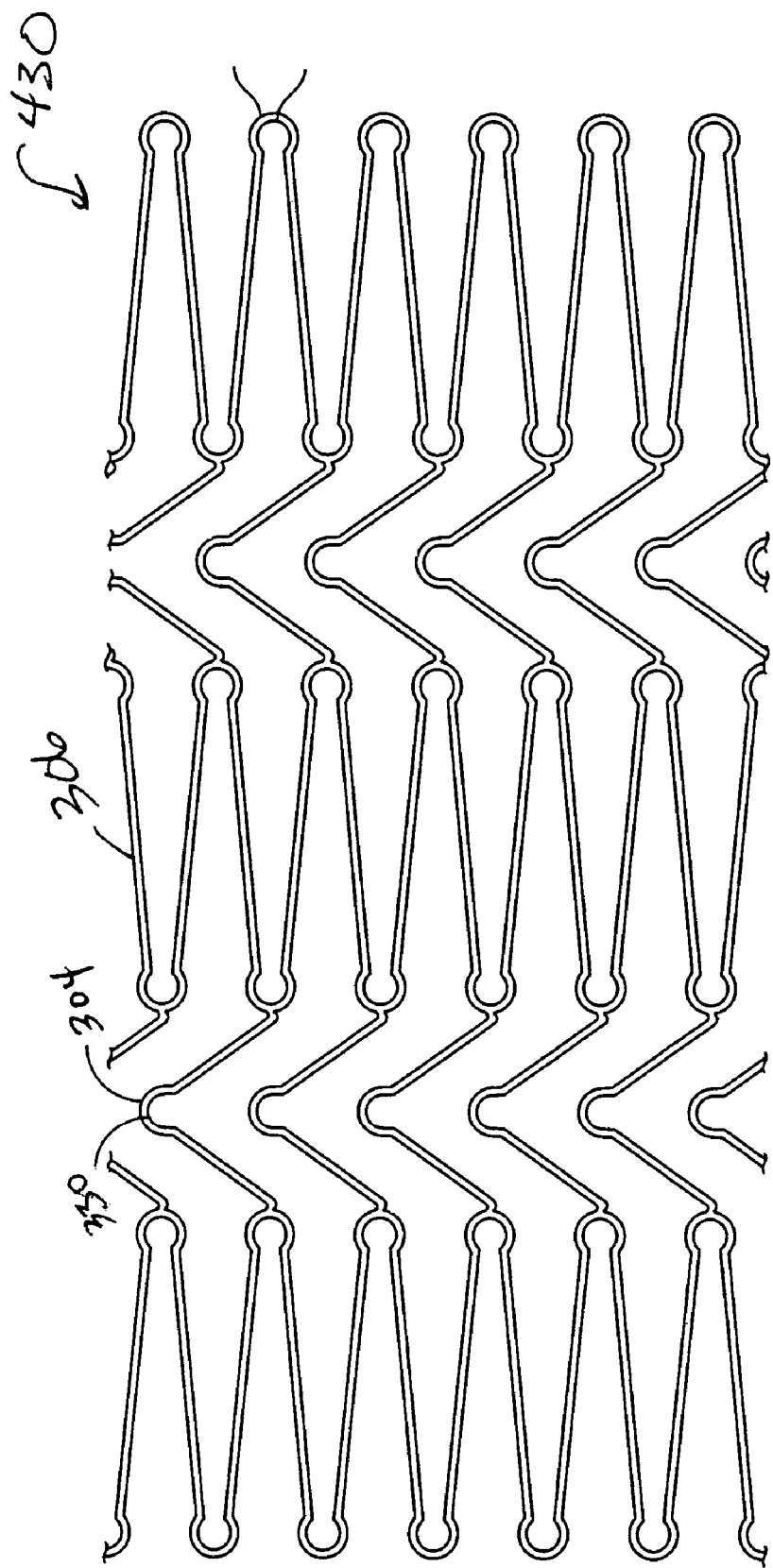
FIG. 38 is a plan view of a structural support element of an alternative embodiment of the implantable endoluminal graft.
Figure 39:
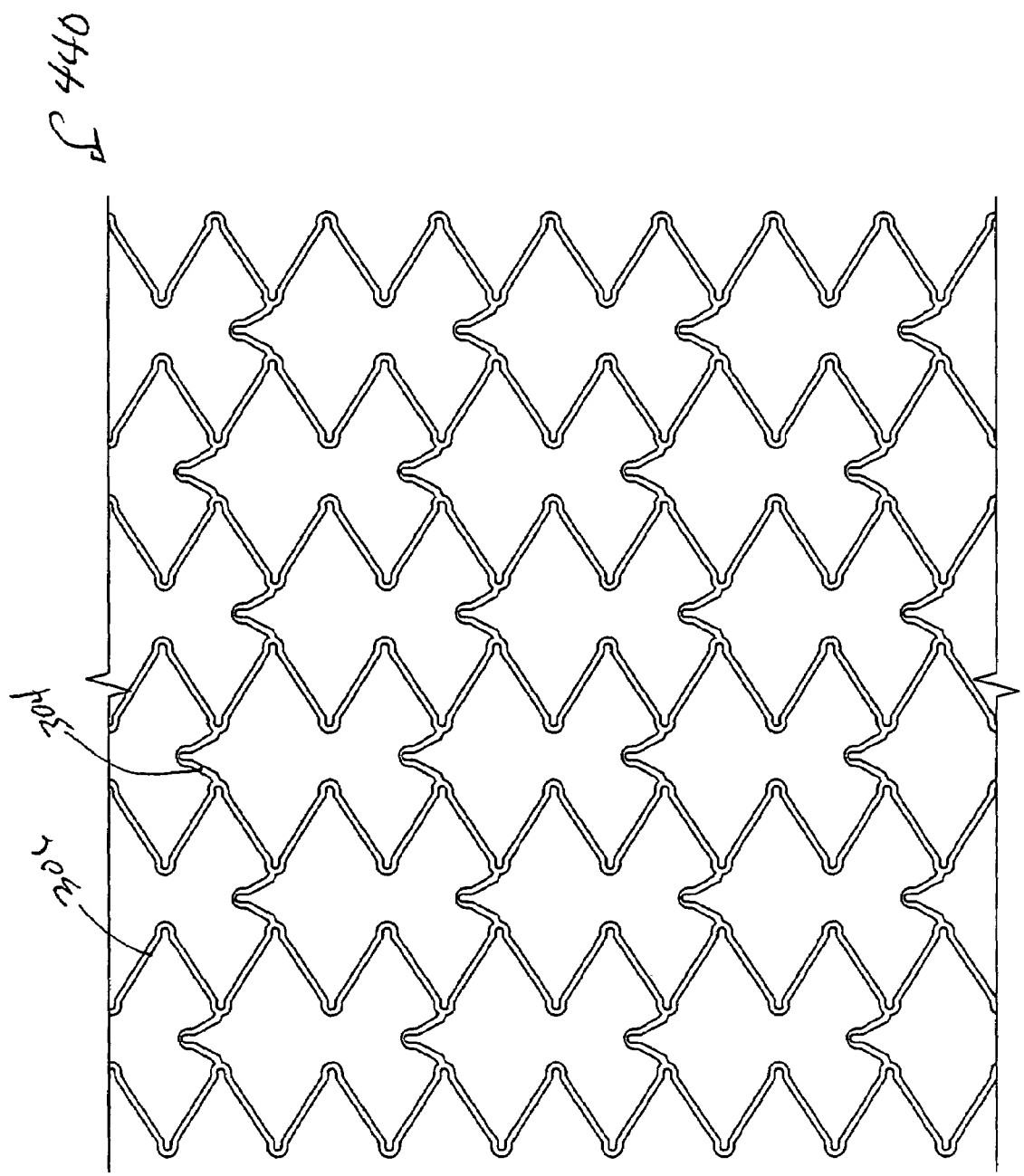
FIG. 39 is a plan view of a structural support element of an alternative embodiment of the implantable endoluminal graft.
Figure 40:
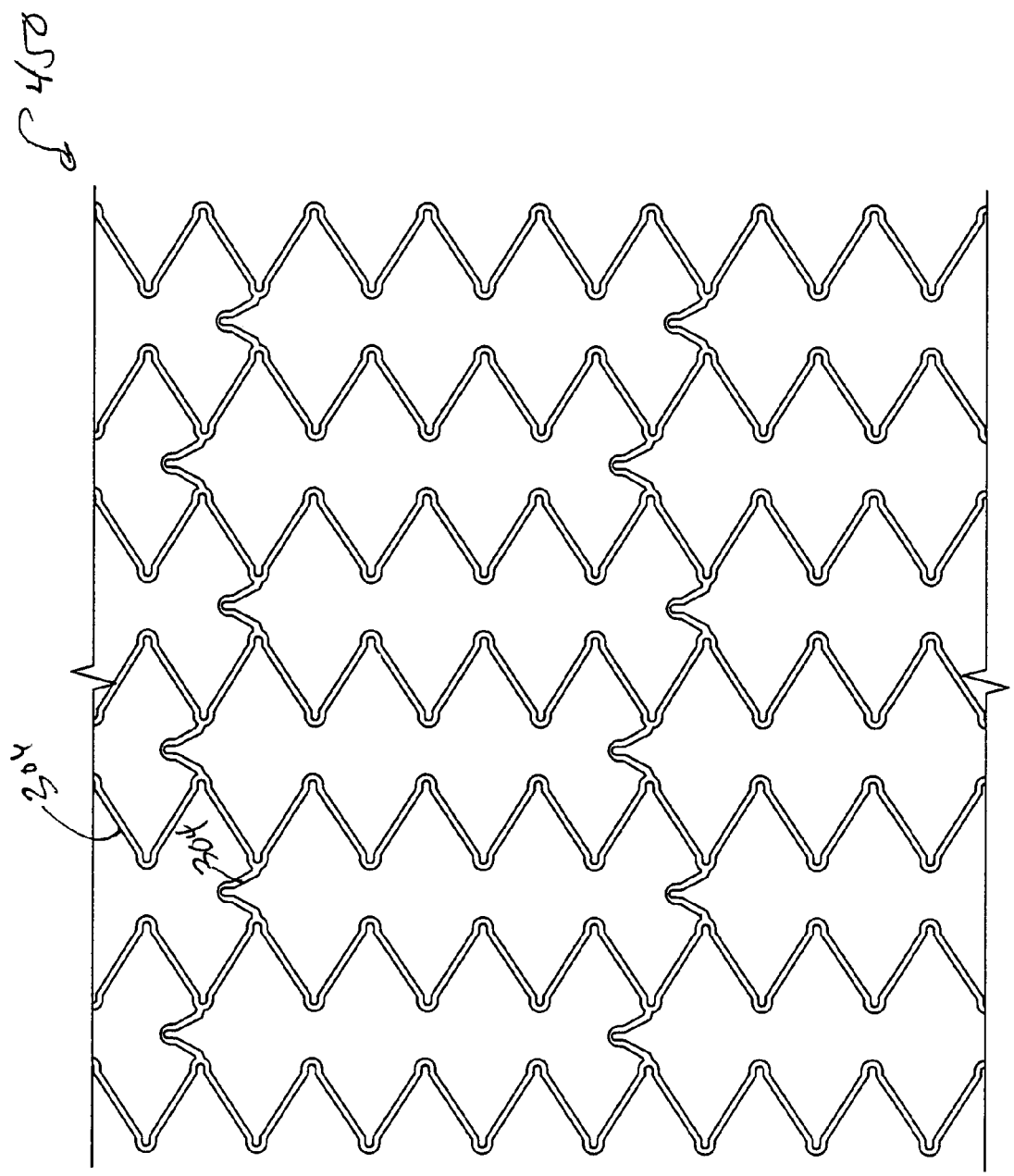
FIG. 40 is a plan view of a structural support element of an alternative embodiment of the implantable endoluminal graft.

As illustrated in FIGS. 28A and 28B, the linear longitudinal interconnecting elements 311 and 312 between adjacent pairs of circumferential elements, may have different lengths which either decreases, in the case of shorter length longitudinal interconnecting elements 311, or increases, in the case of longer longitudinal interconnecting elements 312, the spacing between adjacent pairs of circumferential elements and alters the longitudinal flexibility of the structural support member.

FIGS. 29-33 illustrate alternate embodiments in which the undulating circumferential elements 306 are interconnected by different configurations of interconnecting elements 304, such as non-linear interconnecting elements 304 that have alternate spacing and either connect peak-to-peak or peak-to-valley of the adjacent pairs of undulating circumferential elements 306.

FIGS. 34-40 illustrate alternate embodiments 380, 390, 400, 420, 430, 440, 450 of the structural support member in which the circumferential elements 306 have apices at the peaks and the valleys that have a generally semicircular or C-shape, and each of the interconnecting elements 304 are non-linear bent elements having a generally U-shaped apex intermediate its length. The principal difference between the illustrated alternate embodiments lies in the number and spacing of the interconnecting elements 304.

Figure 41:
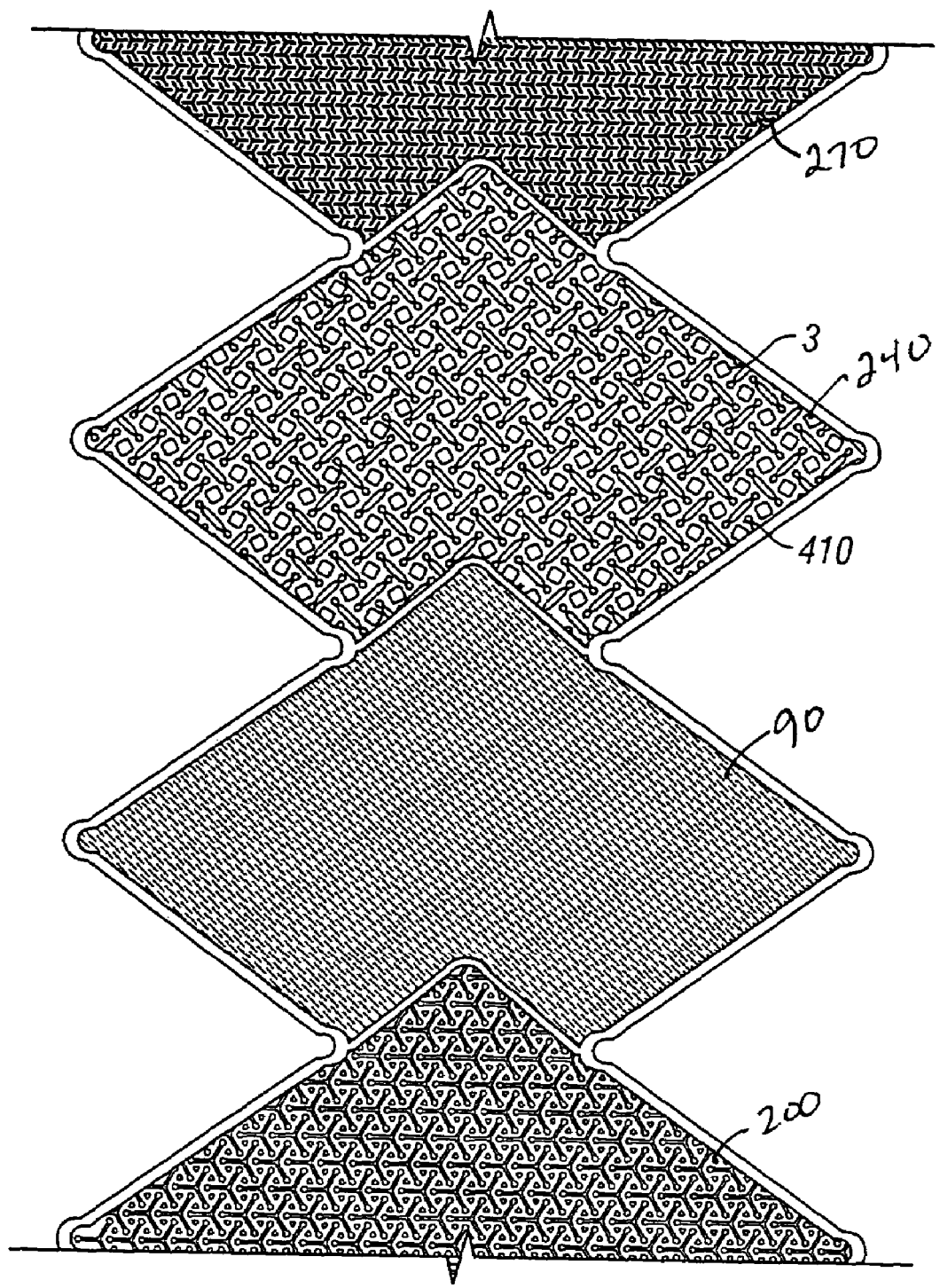
FIG. 41 is a plan view of a structural support element of an alternative embodiment of the implantable endoluminal graft illustrating different patterns of the microporous openings in the microporous metal thin film coverings.

FIG. 41 illustrates an expanded view of a particular geometry of a structural support element with portions of microporous metal thin film coverings 3 shown within the interstices 410. Four different microporous metal thin film coverings 3 are shown that have different opening patterns 200, 90, 240 and 270 as previously described, it being understood that it is preferable in accordance with the preferred embodiment that a single type of opening pattern in the microporous metal thin film material 3 be employed across the entire structural support element. By covering the interstices 410, the microporous metal thin film coverings 3 create continuous microporous surface that limits passage of fine materials through the interstices 410 while acting as a tissue growth scaffold for eliciting a healing response. Based upon the aggregate open areas of the microporous metal thin film coverings 3, the rate of diffusion of cellular and sub-cellular species and fluids through the interstices is altered.

The microporous metal thin film covering 3 may be fabricated of pre-existing conventionally produced wrought materials, such as stainless steel or nitinol hypotubes, or may be fabricated by thin film vacuum deposition techniques. In addition to wrought materials that are made of a single metal or metal alloy, the inventive grafts may be comprised of a monolayer of biocompatible material or of a plurality of layers of biocompatible materials formed upon one another into a self-supporting laminate structure. Laminate structures are generally known to increase the mechanical strength of sheet materials, such as wood or paper products. Laminates are used in the field of thin film fabrication also to increase the mechanical properties of the thin film, specifically hardness and toughness. Laminate metal foils have not been used or developed because the standard metal forming technologies, such as rolling and extrusion, for example, do not readily lend themselves to producing laminate structures. Vacuum deposition technologies can be developed to yield laminate metal structures with improved mechanical properties. In addition, laminate structures can be designed to provide special qualities by including layers that have special properties such as superelasticity, shape memory, radio-opacity, corrosion resistance etc.

According to the preferred method of making the graft of the present invention, the graft is fabricated of vacuum deposited metallic and/or pseudometallic films. A preferred fabrication method of the present invention is described in the following. A precursor blank of a conventionally fabricated biocompatible metal or pseudometallic material, or alternatively, a precursor blank of a vacuum deposited metal or pseudometallic film is employed. Either precursor blank material is then preferably masked, leaving exposed only those regions defining the plurality of openings 31 (see FIG. 4). The exposed regions are then subjected to removal either by etching, such as by wet or dry chemical etching processing, with the etchant being selected based upon the material of the precursor blank, or by machining, such as by laser ablation or EDM. Alternatively, when employing vacuum deposition, a pattern mask corresponding to the plurality of openings may be interposed between the target and the source and the metal or pseudometal deposited through the pattern mask to form the patterned openings. Further, when employing vacuum deposition, plural film layers maybe deposited to form a laminate film structure of the film prior to or concurrently with forming the plurality of openings.

Where a laminate film is fabricated as the graft, it is necessary to provide for good adhesion between the layers. This may be achieved by providing for a relatively broad interfacial region rather than for an abrupt interface. The width of the interface region may be defined as the range within which extensive thermodynamic parameters change. This range can depend on the interface area considered and it may mean the extent of interface microroughness. In other words, adhesion may be promoted by increased interfacial microroughness between adjacent layers within the film. The microroughness may be imparted by chemical or mechanical means, such as chemical etching or laser ablation, or may be included as a process step during vacuum deposition by selectively depositing a metal or pseudometallic species to form the microroughness.

Thus, the present invention provides a new metallic and/or pseudometallic implantable graft that is biocompatible, geometrically changeable either by folding and unfolding or by application of a plastically deforming force, and capable of endoluminal delivery with a suitably small delivery profile. Suitable metal materials to fabricate the inventive membranes are chosen for their biocompatibility, mechanical properties, i.e., tensile strength, yield strength, and their ease of deposition include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Examples of pseudometallic materials potentially useful with the present invention include, for example, composite materials, ceramics, quartz, and borosilicate.

The present invention also provides a method of making the inventive implantable endoluminal graft devices by vacuum deposition of a graft-forming metal or pseudometal and formation of the openings either by removing sections of deposited material, such as by etching, EDM, ablation, or other similar methods, or by interposing a pattern mask, corresponding to the openings, between the target and the source during deposition processing. Alternatively, a pre-existing metal and/or pseudometallic film manufactured by conventional non-vacuum deposition methodologies, such as wrought hypotube, may be obtained, and the micro-openings formed in the pre-existing metal and/or pseudometallic film by removing sections of the film, such as by etching, EDM, ablation, or other similar methods. An advantage of employing laminated film structures to form the inventive graft is that differential functionalities may be imparted in the discrete layers. For example, a radiopaque material such as tantalum may form one layer of a structure while other layers are chosen to provide the graft with its desired mechanical and structural properties.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto.

What is claimed is:

1. An implantable endoluminal graft, comprising:
   (a) a microporous metal thin film covering having a pattern of microporous openings passing therethrough;
   (b) a metal structural support element having at least one affixation member, a pattern of openings passing through the metal structural support element and underlying the microporous metal thin film covering comprised of a metallic material; and
   (c) wherein the metal structural support element is attached to the microporous metal thin film covering only at the at least one affixation member.

2. The implantable endoluminal graft of claim 1, wherein the affixation member is positioned near either a proximal end or distal end of the microporous metal thin film covering and a corresponding end of the metal structural support element.

3. The implantable endoluminal graft of claim 1, wherein the affixation member is near a distal end of the microporous metal thin film covering and metal structural support element.

4. The implantable endoluminal graft according to claim 1, wherein the at least one affixation member is positioned near a terminal end of the metal structural support element.

5. The implantable endoluminal graft of claim 4, wherein the microporous metal thin film covering is attached to the at least one affixation member.

6. The implantable endoluminal graft according to claim 4, wherein the metal structural support element further comprises a plurality of cylindrical elements and interconnecting elements, the cylindrical elements adopting a sinusoidal pattern with alternating peaks and valleys and the at least one affixation member extends longitudinally from at least one of a peak or a valley at a terminal end of the metal structural support element.

7. The implantable endoluminal graft of claim 6, wherein the microporous metal thin film covering exhibits a uniform pattern of openings throughout the surface of the microporous metal thin film covering.

8. The implantable endoluminal graft of claim 7, wherein the microporous metal thin film covering and the metal structural support element are fabricated from nitinol.

9. The implantable endoluminal graft of claim 8, wherein the microporous metal thin film covering maintains a martensite crystalline structure throughout a temperature transition from room temperature to body temperature and behaves martensitically in vivo.

10. The implantable endoluminal graft of claim 8, wherein the metal structural support element undergoes a martensite to austenite phase transition, during a temperature transition from room temperature to body temperature and behaves austenitically in vivo.

11. The implantable endoluminal graft of claim 8, further comprising a microporous metal thin film covering that maintains an austenite crystalline structure throughout a temperature transition from room temperature to body temperature and behaves austenitically in vivo.

12. The implantable endoluminal graft of claim 8, further comprising a microporous metal thin film covering that undergoes a phase transition, from martensite to austenite crystal structure, during a temperature transition from room temperature to body temperature and behaves austenitically in vivo.

13. The implantable endoluminal graft of claim 1, wherein the metal structural support element has a sinusoidal pattern with alternating peaks and valleys.

14. The implantable endoluminal graft of claim 1, wherein the at least one affixation member comprises a projection projecting proximally or distally from a cylindrical element at a terminal end of the structural support member.

15. An implantable endoluminal graft, comprising:
(a) a microporous metal thin film covering comprised of a shape memory alloy having an austenite phase transition start temperature greater than 37° C. and the microporous metal thin film covering having a pattern of microporous openings passing therethrough; and
(b) a structural support element underlying the microporous covering comprised of at least a pair of cylindrical elements and interconnecting members joining adjacent cylindrical elements, the structural support element further comprised of a shape memory alloy having an austenite phase transition start temperature less than 0° C.;
(c) the structural support element being attached to the microporous metal thin film covering at least one point of attachment including an at least one affixation member between the microporous metal thin film covering and the structural support element.

16. The implantable endoluminal graft of claim 15, wherein the shape memory alloy is nitinol.

17. The implantable endoluminal graft of claim 15, wherein the microporous metal thin film covering maintains a martensite crystalline structure throughout the temperature transition from room temperature to body temperature.

18. The implantable endoluminal graft of claim 15, further comprising a structural support member that undergoes a phase transition, from martensite to austenite crystal structure, during the temperature transition from room temperature to body temperature.

19. The implantable endoluminal graft of claim 15, wherein the at least one affixation member is located at either near a proximal end or distal end of the microporous metal thin film covering and corresponding end of the structural support element.

20. The implantable endoluminal graft of claim 15, wherein the at least one affixation member is located at near a distal end of the microporous metal thin film covering and structural support element.

21. The implantable endoluminal graft of claim 15, wherein the cylindrical elements adopt a sinusoidal pattern with alternating peaks and valleys.

22. The implantable endoluminal graft of claim 15, wherein the pattern of microporous openings exhibits a uniform pattern of openings throughout the surface of the microporous metal thin film covering.

23. The implantable endoluminal graft of claim 15, wherein the at least one affixation member is on a terminal end of a terminal interconnecting member.

24. An implantable endoluminal graft, comprising:
a. a microporous metal thin film covering comprised of nitinol; and
b. a structural support element underlying the microporous covering comprised of at least a pair of undulating cylindrical elements having a plurality of peaks and valleys and interconnecting members joining adjacent cylindrical elements at either the peaks or the valleys and having at least one projection extending longitudinally from a terminal cylindrical element, the structural support element being comprised of nitinol,
c. the structural support element being joined to the microporous metal thin film covering at the at least one projection.

25. The implantable endoluminal graft of claim 24, wherein the microporous metal thin film covering maintains a martensite crystalline structure throughout the temperature transition from room temperature to body temperature.

26. The implantable endoluminal graft of claim 24, wherein the structural support member that undergoes a phase transition, from martensite to austenite crystal structure, during the temperature transition from room temperature to body temperature.

27. The implantable endoluminal graft of claim 24, further comprising a microporous metal thin film covering that maintains an austenite crystalline structure throughout a temperature transition from room temperature to body temperature and behaves austenitically in vivo.

28. The implantable endoluminal graft of claim 24, further comprising a microporous metal thin film covering that undergoes a phase transition, from martensite to austenite crystal structure, during a temperature transition from room temperature to body temperature and behaves austenitically in vivo.

29. The implantable endoluminal graft of claim 24, wherein the microporous metal thin film covering exhibits a regular pattern of openings throughout a surface of the microporous metal thin film covering.

30. The implantable endoluminal graft of claim 29, wherein the regular pattern of openings further comprises a plurality of elongate slots arrayed in circumferentially adjacent and longitudinally offset rows, each of the plurality of elongate slots being parallel to a longitudinal axis of the endoluminal graft and capable of opening under the influence of a circumferentially expansive force.

* * * * *